United States Patent
Sasaki et al.

(10) Patent No.: US 12,207,875 B2
(45) Date of Patent: Jan. 28, 2025

(54) EYE MOVEMENT ANALYSIS SYSTEM, EYE MOVEMENT ANALYSIS METHOD AND PROGRAM

(71) Applicant: TEIKYO UNIVERSITY, Tokyo (JP)

(72) Inventors: Kakeru Sasaki, Tokyo (JP); Takao Hayashi, Tokyo (JP)

(73) Assignee: TEIKYO UNIVERSITY, Tokyo (JP)

( * ) Notice: Subject to any disclaimer, the term of this patent is extended or adjusted under 35 U.S.C. 154(b) by 721 days.

(21) Appl. No.: 17/433,086

(22) PCT Filed: Mar. 2, 2020

(86) PCT No.: PCT/JP2020/008573
§ 371 (c)(1),
(2) Date: Aug. 23, 2021

(87) PCT Pub. No.: WO2020/179720
PCT Pub. Date: Sep. 10, 2020

(65) Prior Publication Data
US 2022/0087524 A1 Mar. 24, 2022

(30) Foreign Application Priority Data
Mar. 4, 2019 (JP) ................. 2019-038941

(51) Int. Cl.
*A61B 3/113* (2006.01)
*G06F 3/01* (2006.01)
(Continued)

(52) U.S. Cl.
CPC .............. *A61B 3/113* (2013.01); *G06F 3/013* (2013.01); *G06F 3/0346* (2013.01); *G06T 7/20* (2013.01)

(58) Field of Classification Search
CPC .......... G02B 27/017; G02B 2027/0138; G02B 2027/014; G02B 2027/0187; G02B 27/0172; G02B 2027/0178; G02B 2027/0118; G02B 27/0093; G02B 27/0179; G02B 6/00; G02B 6/0088; G02B 2027/0181; G02B 2027/0112;
(Continued)

(56) References Cited

U.S. PATENT DOCUMENTS 4,891,630 A 1/1990 Friedman et al.

FOREIGN PATENT DOCUMENTS

JP 02-224637 A 9/1990
JP 11-225967 A 8/1999
(Continued)

OTHER PUBLICATIONS

International Search Report, PCT/JP2020/008573, Apr. 14, 2020, 4 pgs.

*Primary Examiner* — Brandi N Thomas
(74) *Attorney, Agent, or Firm* — Volpe Koenig

(57) ABSTRACT

An eye movement analysis system includes an image-capturing unit configured to capture a moving image including at least one of a right eye and a left eye of a subject and a comparison target on a surface of a face of the subject, and an analysis unit configured to analyze a movement of an eyeball of the at least one of the right eye and the left eye of the subject, based on a relationship between the at least one of the right eye and the left eye of the subject and the comparison target on the moving image captured by the image-capturing unit.

17 Claims, 9 Drawing Sheets

(51) Int. Cl.
*G06F 3/0346* (2013.01)
*G06T 7/20* (2017.01)

(58) Field of Classification Search
CPC ........ G02B 2027/0134; G02B 26/0875; G02B 27/0176; G02B 2027/0141; G02B 30/25; G02B 30/27; G02B 30/33; G02B 7/285; H04N 13/239; H04N 13/344; H04N 13/243; H04N 13/296; H04N 23/63; H04N 5/445; H04N 7/181; H04N 13/383; H04N 23/60; H04N 5/45; H04N 7/185; H04N 23/611; H04N 7/18; H04N 13/111; H04N 13/398; H04N 23/62; H04N 23/90; H04N 13/189; H04N 13/204; H04N 23/69; H04N 13/221; H04N 2013/0081; H04N 23/00; H04N 23/682; H04N 25/61; H04N 5/2622; H04N 1/00201; H04N 13/10; H04N 13/128; H04N 13/139; H04N 13/161; H04N 13/194; H04N 13/275; H04N 13/286; H04N 13/30; H04N 13/302; H04N 13/305; H04N 13/307; H04N 13/31; H04N 13/32; H04N 13/324; H04N 13/327; H04N 13/341; H04N 13/346; H04N 13/349; H04N 13/363; H04N 13/366; H04N 13/368; H04N 13/373; H04N 13/376; H04N 13/38; H04N 19/597; H04N 23/51; H04N 23/61; H04N 23/635; H04N 23/67; H04N 23/70; H04N 23/74; H04N 5/262; A61B 3/113; A61B 5/163; A61B 5/4863; A61B 3/0025; A61B 3/08; A61B 3/145; A61B 17/155; A61B 17/157; A61B 17/1666; A61B 17/1703; A61B 17/1746; A61B 2017/00207; A61B 2034/102; A61B 2034/105; A61B 2034/107; A61B 2034/108; A61B 2034/2065; A61B 2090/365; A61B 2090/372; A61B 2090/3983; A61B 3/111; A61B 34/10; A61B 5/05; A61B 5/1104; A61B 5/1107; A61B 5/1128; A61B 5/14535; A61B 5/16; A61B 5/441; A61B 5/4884; A61B 5/7267; A61B 90/37

See application file for complete search history.

(56) References Cited

FOREIGN PATENT DOCUMENTS

| | | | | |
|---|---|---|---|---|
| JP | 2004-167152 | A | 6/2004 | |
| JP | 2005-323905 | A | 11/2005 | |
| JP | 2006-285531 | A | 10/2006 | |
| JP | 2006285531 | | * 10/2006 | ................ A61B 3/10 |
| WO | WO 2013175037 | | * 11/2013 | ............ G02B 27/017 |

\* cited by examiner

EYE MOVEMENT ANALYSIS SYSTEM, EYE MOVEMENT ANALYSIS METHOD AND PROGRAM

TECHNICAL FIELD

The present invention relates to an eye movement analysis system, an eye movement analysis method, and a program.

Priority is claimed on Japanese Patent Application No. 2019-038941, filed Mar. 4, 2019, the content of which is incorporated herein by reference.

BACKGROUND ART

Nystagmus is a disease in which the eyeball repeatedly reciprocates regularly and continuously regardless of its own will. Nystagmus also seen in healthy people under special conditions, but in pathological nystagmus, what is seen may appear to shake depending on the degree of eye shaking, or eyesight may deteriorate due to shaking of a retinal image, which may lead to problems in daily life.

More than 90% of pathological nystagmus is nystagmus that is born (congenital nystagmus). Congenital nystagmus includes infantile nystagmus, congenital alternating nystagmus, (manifest) latent nystagmus, nystagmus blockage syndrome, and spasms nutans. Most exhibit nystagmus that sways horizontally (left and right).

For the analysis of nystagmus, nystagmus analysis is generally used in which the movement of the eye is represented as a vertical waveform (the movement of the eye to the right is up and the movement of the eye to the left is down). The nystagmus waveform consists of three important components.

When classified by the type of nystagmus (speed change of going (slow phase) and returning (fast phase)), nystagmus is classified into pendular nystagmus, jerk nystagmus (slow phase velocity increase type), and jerk nystagmus (slow phase velocity decrease type).

When classified by the magnitude (amplitude) of the shaking, nystagmus is classified into a large amplitude and a small amplitude. Nystagmus of small amplitude often has better visual function than nystagmus of large amplitude.

When classified by frequency (frequency: number of round trips per second), nystagmus is classified into high frequency and low frequency. Nystagmus of low frequency often has better visual function than nystagmus of high frequency.

Since the causative diseases and treatment methods differ depending on the type of nystagmus, it is very important to accurately classify nystagmus in order to properly perform diagnosis and treatment. In addition, since the magnitude of amplitude and the frequency of shaking are directly related to the visual function, they are criteria for determining the necessity of treatment and the treatment method.

From the above, it is extremely necessary to perform qualitative and quantitative analysis of nystagmus.

Currently, there are two types of methods implemented as methods for analyzing nystagmus: electronystagmogram and a scleral search coil technique.

Electronystagmogram is the mainstream of nystagmus tests. In electronystagmogram, electrodes are placed around the eye to measure the nystagmus by detecting the potential change due to the nystagmus. Since many measurement electrodes are attached to the face, the subject has a strong discomfort. Another problem is that precise calibration is required before the test, and the electromyogram due to the tension and strength of the subject is mixed into the waveform as an artifact.

In the scleral search coil technique, a contact lens with an embedded electrode (coil) is placed in the eye in a special space where a magnetic field is generated, and nystagmus is measured by capturing the potential change caused by the movement of the contact lens. The scleral search coil technique has the highest accuracy and enables detailed waveform analysis, but has problems in that it is extremely invasive and requires a large space and a large-scale magnetic field generator.

Both test methods have the fatal disadvantage that it is difficult to test children, the majority of nystagmus patients, who are the main targets of nystagmus test. Therefore, it is difficult to analyze nystagmus in detail in children, and the pathological condition of the nystagmus has not been elucidated at present. Clinically, it is extremely difficult to classify the type of congenital nystagmus and determine an appropriate treatment policy.

Further, videonystagmography (VNG) has been known in the related art. In VNG, nystagmus is measured using an infrared camera. VNG is mainly used for diagnosing dizziness in the field of otolaryngology. Since VNG is based on the Purkinje image, its accuracy is limited and cannot be used for detailed waveform analysis. In addition, it is difficult to measure in children because they need to wear specialized large goggles.

Further, in the related art, an analysis method has been known in which the angular velocity of the eyeball is calculated from an image of the eyeball by using a computer, and the eye movement is quantitatively observed (see, for example, Patent Document 1). In the technique described in Patent Document 1, an image of an eyeball output from an imaging camera in the form of a video signal is AD-converted, and captured as image data.

Incidentally, in the technique described in Patent Document 1, a goggle-type eyeball observation fittings are used. That is, in the technique described in Patent Document 1, the movement of the eyeball is analyzed while the distance between the imaging camera and the eyeball of the subject is maintained constant. Therefore, depending on the technique described in Patent Document 1, it is not possible to analyze the movement of the eyeball of the subject with high accuracy, when the distance between the imaging camera and the eyeball of the subject changes.

Further, in the related art, an eye movement measuring device including an eyeball image-capturing camera that captures the image of the eyeball of a subject, and an eyeball tracking unit that tracks the position of the eyeball from an image captured by the eyeball image-capturing camera has been known (for example, see Patent Document 2).

Incidentally, in the technique described in Patent Document 2, although it is not necessary to maintain a constant distance between the eyeball image-capturing camera and the eyeball of the subject, it is necessary to provide a subject image-capturing camera separately from the eyeball image-capturing camera. Further, in the technique described in Patent Document 2, calibration needs to be performed in advance.

CITATION LIST

Patent Documents

[Patent Document 1]

Japanese Unexamined Patent Application, First Publication No. H11-225967

[Patent Document 2]
Japanese Unexamined Patent Application, First Publication No. 2005-323905

SUMMARY OF INVENTION

Technical Problem

Eye-gaze analysis is a method of detecting the position of the eye and the movement of the line-of-sight, by projecting and analyzing the relative positional relationship between the specular reflection image (Purkinje image) projected on the cornea by using an infrared light source and the pupil with an infrared camera. Specifically, in the eye-gaze analysis method, an infrared light is applied to the cornea of the subject to create a Purkinje image on the surface of the cornea, and the movement of the line-of-sight is analyzed from the relative positional relationship with the center of gravity of the pupil.

The present inventors have attempted to measure nystagmus in pediatric nystagmus patients using a calibration-free eye-gaze analyzer. As a result, some measurement has been made possible, but problems such as the obtained waveform being unstable and poorly reproducible, and the waveform being greatly disturbed and unmeasurable when the patient's head moves even a little cannot be solved, which cannot lead to a nystagmus analysis that can withstand clinical use.

Analysis of these causes reveals that the cornea is not a perfect sphere, and the position of the Purkinje image changes when looking at the center and periphery, resulting in poor accuracy.

In addition, since the tear film on the outermost surface of the cornea is constantly fluctuating (swaying), the Purkinje image projected on the cornea becomes unstable (always fluctuating), causing minute measurement errors (it is measured as if there is a slight shaking even though the eyes are not moving). In other words, it has become clear that it is difficult to improve the analysis accuracy by this method.

In addition, in this method, it has become clear that it is not possible to distinguish between eye movements and the movements of the face itself, and if the face of the subject moves during the measurement, it is inevitable that the movement is erroneously detected as the movement of the line-of-sight.

Further, in this method, it is necessary to perform precise calibration before measurement, and the measured value changes greatly when the distance between the infrared camera and the subject changes.

That is, although this method is suitable for rough analysis of line-of-sight, it has a drawback that it is not suitable for detecting fine eye movements such as nystagmus.

Therefore, the present inventors have found a method to eliminate these drawbacks, instead of using the Purkinje image which has been considered to be indispensable for tracking the line-of-sight from the image, but by attaching a reference comparison target to the surface of the face of the subject, or using the morphological features (for example, moles) on the surface of the face of the subject as comparison targets.

In addition, the present inventors have found that this method can also be used not only for analysis of pathological nystagmus, but also for analysis of physiological nystagmus (nystagmus that occurs under specific conditions even in normal subjects), dizziness, vibration of the eyeball due to ear and brain diseases, comitant strabismus, incomitant strabismus (ocular motility disorder), gaze paralysis, or the like, eye movement analysis of normal people, fixation tremor analysis, or the like. In detail, the present inventors have considered that by using this method, it is possible to examine the difference in the movement of the right eye and the left eye when the movement of the eye is impaired due to paralysis of the ocular nerve.

That is, an object of the present invention is to provide an eye movement analysis system, an eye movement analysis method, and a program, capable of analyzing the movement of the eyeball of a subject with high accuracy, even when the distance between the image-capturing unit and the subject changes, without the use of a Purkinje image and without performing calibration in advance.

Solution to Problem

One aspect of the present invention is an eye movement analysis system including: an image-capturing unit configured to capture a moving image including at least one of a right eye and a left eye of a subject and a comparison target on a surface of a face of the subject; and an analysis unit configured to analyze a movement of an eyeball of the at least one of the right eye and the left eye of the subject, based on a relationship between the at least one of the right eye and the left eye of the subject and the comparison target on the moving image captured by the image-capturing unit.

In the eye movement analysis system of one aspect of the present invention, the comparison target may be a sticker attached between eyebrows of the subject.

The eye movement analysis system of one aspect of the present invention may further include an acquisition unit configured to acquire information of the comparison target, wherein the analysis unit may analyze the movement of the eyeball of the at least one of the right eye and the left eye of the subject, based on an actual size of the comparison target acquired by the acquisition unit, a dimension of the comparison target on the moving image captured by the image-capturing unit, and a distance between the at least one of the right eye and the left eye of the subject and the comparison target on the moving image captured by the image-capturing unit.

In the eye movement analysis system of one aspect of the present invention, an actual size of a distance between a plurality of points on the comparison target may be used as the actual size of the comparison target, and a dimension between the plurality of points on the comparison target on the moving image may be used as the dimension of the comparison target on the moving image.

In the eye movement analysis system of one aspect of the present invention, the comparison target may be circular, and the analysis unit may analyze the movement of the eyeball of the right eye of the subject, based on an actual size of a diameter or radius of the comparison target acquired by the acquisition unit, the diameter or radius of the comparison target on the moving image captured by the image-capturing unit, and a distance between a point on the right eye of the subject and a center of the comparison target on the moving image captured by the image-capturing unit, and analyze the movement of the eyeball of the left eye of the subject, based on the actual size of the diameter or radius of the comparison target acquired by the acquisition unit, the diameter or radius of the comparison target on the moving image captured by the image-capturing unit, and a distance between a point on the left eye of the subject and the center of the comparison target on the moving image captured by the image-capturing unit.

In the eye movement analysis system of one aspect of the present invention, the point on the right eye of the subject on the moving image may be a center of a pupil of the right eye of the subject on the moving image, and the point on the left eye of the subject on the moving image may be a center of a pupil of the left eye of the subject on the moving image.

In the eye movement analysis system of one aspect of the present invention, the point on the right eye of the subject on the moving image may be a point on an iris of the right eye of the subject on the moving image, and the point on the left eye of the subject on the moving image may be a point on an iris of the left eye of the subject on the moving image.

In the eye movement analysis system of one aspect of the present invention, the point on the right eye of the subject on the moving image may be a point on a conjunctival blood vessel of the right eye of the subject on the moving image, and the point on the left eye of the subject on the moving image may be a point on a conjunctival blood vessel of the left eye of the subject on the moving image.

In the eye movement analysis system of one aspect of the present invention, the comparison target may be a polygon, and the analysis unit may analyze the movement of the eyeball of the right eye of the subject, based on an actual size of a distance between two vertices of the polygon of the comparison target acquired by the acquisition unit, a distance between the two vertices of the polygon of the comparison target on the moving image captured by the image-capturing unit, and a positional relationship between a point on the right eye of the subject and the two vertices of the polygon of the comparison target on the moving image captured by the image-capturing unit, and analyze the movement of the eyeball of the left eye of the subject, based on the actual size of the distance between two vertices of the polygon of the comparison target acquired by the acquisition unit, the distance between the two vertices of the polygon of the comparison target on the moving image captured by the image-capturing unit, and a positional relationship between a point on the left eye of the subject and the two vertices of the polygon of the comparison target on the moving image captured by the image-capturing unit.

In the eye movement analysis system of one aspect of the present invention, the comparison target may be a polygon, and the analysis unit may analyze the movement of the eyeball of the right eye of the subject, based on an actual size of a distance between two vertices of the polygon of the comparison target acquired by the acquisition unit, the distance between the two vertices of the polygon of the comparison target on the moving image captured by the image-capturing unit, and a positional relationship between two points on the right eye of the subject and the two vertices of the polygon of the comparison target on the moving image captured by the image-capturing unit, and analyze the movement of the eyeball of the left eye of the subject, based on the actual size of the distance between two vertices of the polygon of the comparison target acquired by the acquisition unit, the distance between the two vertices of the polygon of the comparison target on the moving image captured by the image-capturing unit, and a positional relationship between two points on the left eye of the subject and the two vertices of the polygon of the comparison target on the moving image captured by the image-capturing unit.

In the eye movement analysis system of one aspect of the present invention, the comparison target may be a morphological feature on the surface of the face of the subject, and the analysis unit may analyze the movement of the eyeball of the at least one of the right eye and the left eye of the subject, based on a relationship between the at least one of the right eye and the left eye of the subject and two points on the comparison target on the moving image captured by the image-capturing unit.

In the eye movement analysis system of one aspect of the present invention, the analysis unit may analyze the movement of the eyeball of the right eye of the subject, based on a distance between the two points on the comparison target on the moving image captured by the image-capturing unit, and a positional relationship between a point on the right eye of the subject and the two points on the comparison target on the moving image captured by the image-capturing unit, and analyze the movement of the eyeball of the left eye of the subject, based on the distance between two points on the comparison target on the moving image captured by the image-capturing unit, and a positional relationship between a point on the left eye of the subject and the two points on the comparison target on the moving image captured by the image-capturing unit.

In the eye movement analysis system of one aspect of the present invention, the sticker as the comparison target may be attached to the subject such that an inclination of a face of the subject is determined from the moving image captured by the image-capturing unit.

In the eye movement analysis system of one aspect of the present invention, the analysis unit may determine the inclination of the face of the subject from the moving image captured by the image-capturing unit, by using at least two points on the sticker.

In the eye movement analysis system of one aspect of the present invention, the analysis unit may determine the inclination of the face of the subject from the moving image captured by the image-capturing unit, by using a positional relationship between a plurality of stickers attached as the comparison target.

The eye movement analysis system of one aspect of the present invention may further include a display unit configured to display an optotype presented to the subject; and a moving unit configured to integrally move the display unit and the image-capturing unit.

One aspect of the present invention is an eye movement analysis method including: an image-capturing step of image-capturing a moving image including at least one of a right eye and a left eye of a subject and a comparison target on a surface of a face of the subject; and an analysis step of analyzing a movement of an eyeball of the at least one of the right eye and the left eye of the subject, based on a relationship between the at least one of the right eye and the left eye of the subject and the comparison target on the moving image captured in the image-capturing step.

One aspect of the present invention is a program causing a computer to execute: an image-capturing step of image-capturing a moving image including at least one of a right eye and a left eye of a subject and a comparison target on a surface of a face of the subject; and an analysis step of analyzing a movement of an eyeball of the at least one of the right eye and the left eye of the subject, based on a relationship between the at least one of the right eye and the left eye of the subject and the comparison target on the moving image captured in the image-capturing step.

Advantageous Effects of Invention

According to the present invention, it is possible to provide an eye movement analysis system, an eye movement analysis method, and a program, capable of analyzing the movement of the eyeball of a subject with high accuracy, even when the distance between the image-capturing unit and the subject changes, without the use of a Purkinje image and without performing calibration in advance.

DESCRIPTION OF EMBODIMENTS

Hereinafter, embodiments of an eye movement analysis system, an eye movement analysis method, and a program of the present invention will be described with reference to the drawings.

First Embodiment

Figure 1:
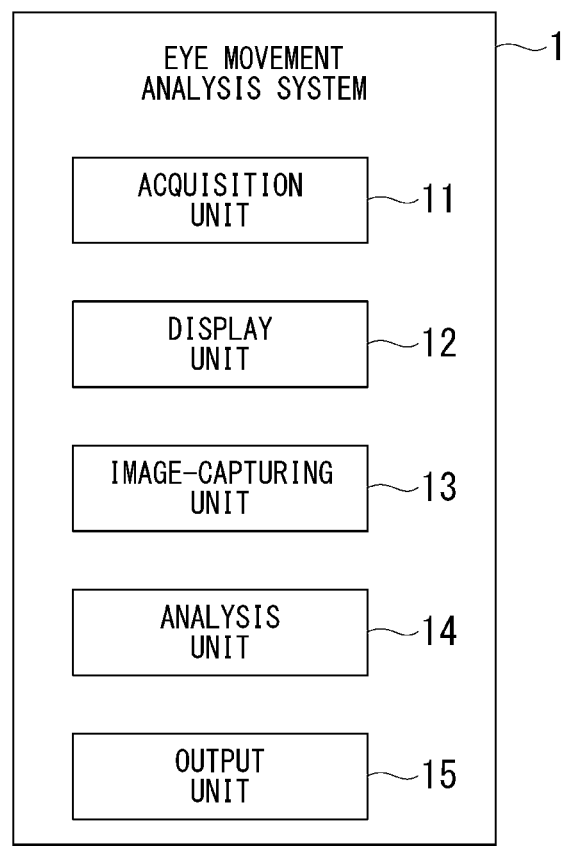
FIG. 1 is a diagram showing an example of the configuration of an eye movement analysis system of a first embodiment.
Figure 2A:
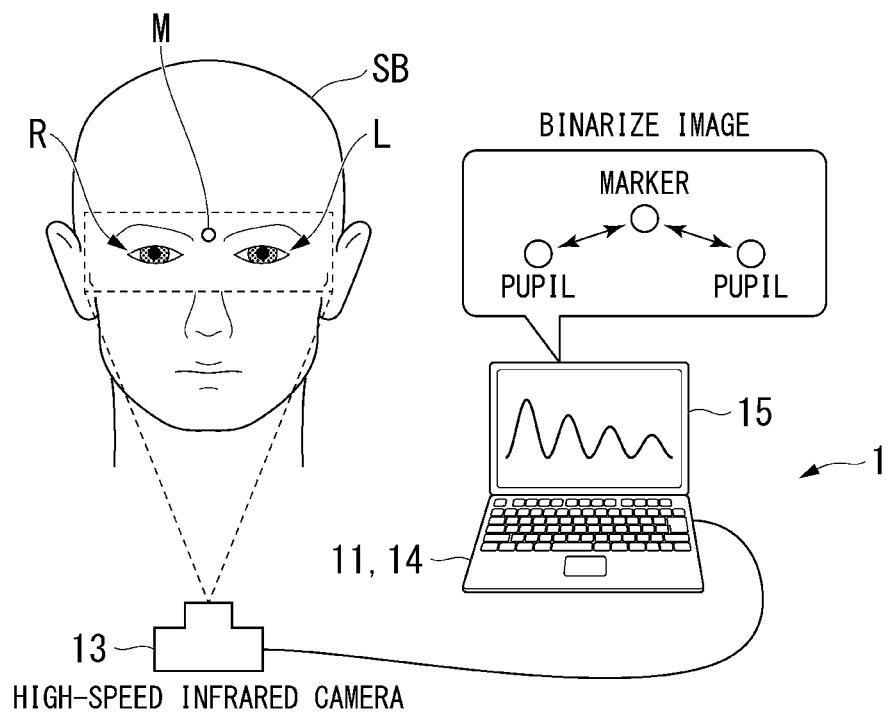
FIGS. 2A and 2B are diagrams showing a first application example of the eye movement analysis system of the first embodiment.
Figure 2B:
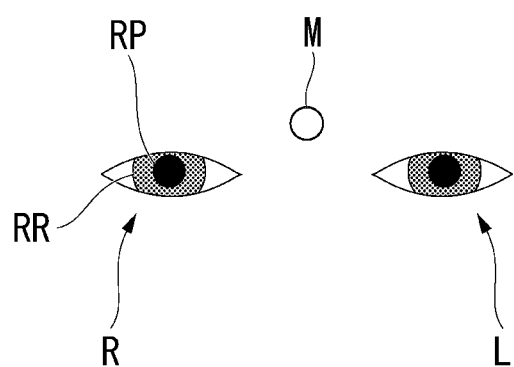

FIG. 1 is a diagram showing an example of the configuration of an eye movement analysis system 1 of a first embodiment. FIGS. 2A and 2B are diagrams showing a first application example of the eye movement analysis system 1 of the first embodiment. In detail, FIG. 2A shows an example of the relationship between the eye movement analysis system 1 and a subject SB in the first application example, and FIG. 2B shows an example of the relationship between the right eye R and the left eye L of the subject SB and a comparison target M.

In the example shown in FIG. 1, the eye movement analysis system 1 of the first embodiment includes an acquisition unit 11, a display unit 12, an image-capturing unit 13, an analysis unit 14, and an output unit 15.

The acquisition unit 11 acquires information of the comparison target M attached to the surface of the face of the subject SB (see FIG. 2A). The comparison target M is a sticker attached between eyebrows of the subject SB.

In another example (for example, an example in which the image-capturing unit 13 captures the images of only one eye of the subject SB and the comparison target M), the comparison target M may be attached to a place other than the place between the eyebrows of the subject SB (for example, a place directly below the eye to be captured).

In the examples shown in FIGS. 1, 2A and 2B, the comparison target M is circular. The information of the comparison target M acquired by the acquisition unit 11 includes the actual size of the diameter or radius of the comparison target M.

In another example, the comparison target M may have a shape other than circular.

In the example shown in FIG. 1, the display unit 12 displays an optotype.

In another example, the eye movement analysis system 1 may not include the display unit 12. In this example (for example, the example shown in FIGS. 2A and 2B), the image-capturing unit 13 functions as the optotype presented to the subject SB.

In the example shown in FIG. 1, the image-capturing unit 13 captures a moving image including the right eye R and the left eye L of the subject SB (see FIG. 2A) and the comparison target M.

The analysis unit 14 analyzes the movements of the eyeballs of the right eye R and left eye L of the subject SB, based on the information of the comparison target M acquired by the acquisition unit 11 and the relationship between the right eye R and left eye L of the subject SB and the comparison target M on the moving image captured by the image-capturing unit 13.

Specifically, the analysis unit 14 analyzes the movement of the eyeball of the right eye R of the subject SB, based on the actual size (the unit is, for example, millimeters) of the comparison target M acquired by the acquisition unit 11, the dimensions (the unit is, for example, pixel) of the comparison target M on the moving image captured by the image-capturing unit 13, and the distance (the unit is, for example, pixel) between the right eye R of the subject SB and the comparison target M on the moving image captured by the image-capturing unit 13. Further, the analysis unit 14 analyzes the movement of the eyeball of the left eye L of the subject SB, based on the actual size (the unit is, for example, millimeters) of the comparison target M acquired by the acquisition unit 11, the dimensions (the unit is, for example, pixel) of the comparison target M on the moving image captured by the image-capturing unit 13, and the distance (the unit is, for example, pixel) between the left eye L of the subject SB and the comparison target M on the moving image captured by the image-capturing unit 13.

The output unit 15 outputs the analysis result by the analysis unit 14. Specifically, the output unit 15 outputs the analysis result of the movement of the eyeball of the right eye R and the analysis result of the movement of the eyeball of the left eye L of the subject SB.

In the example shown in FIG. 2A, the output unit 15 displays the analysis result by the analysis unit 14, but in another example, the output unit 15 may print the analysis result by the analysis unit 14.

Figure 3:
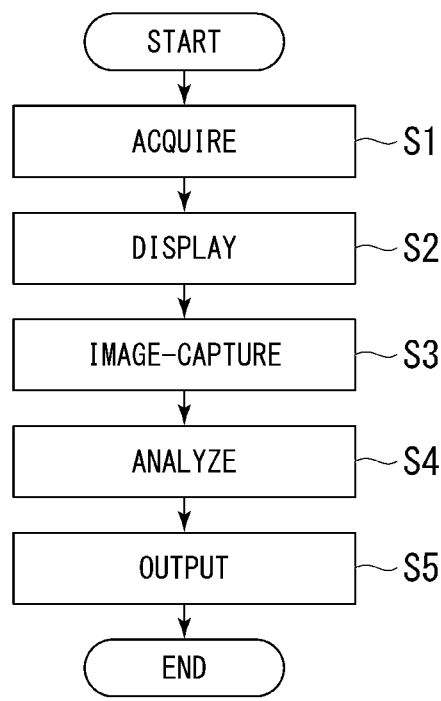
FIG. 3 is a flowchart for explaining an example of a process executed in the eye movement analysis system of the first embodiment.

FIG. 3 is a flowchart for explaining an example of a process executed in the eye movement analysis system 1 of the first embodiment.

In the example shown in FIG. 3, in step S1, the acquisition unit 11 acquires the information of the comparison target M attached to the surface of the face of the subject SB.

Further, in step S2, the display unit 12 displays an optotype.

Next, in step S3, the image-capturing unit 13 captures a moving image including the right eye R and the left eye L of the subject SB and the comparison target M.

Next, in step S4, based on the information of the comparison target M acquired in step S1 and the relationship between the right eye R and left eye L of the subject SB and the comparison target M on the moving image captured in step S3, the movements of the eyeballs of the right eye R and left eye L of the subject SB are analyzed.

Next, in step S5, the output unit 15 outputs the result of the analysis executed in step S4.

In the example shown in FIG. 3, step S2 is executed in the eye movement analysis system 1, but in other examples, step S2 may not be executed.

Figure 4A:
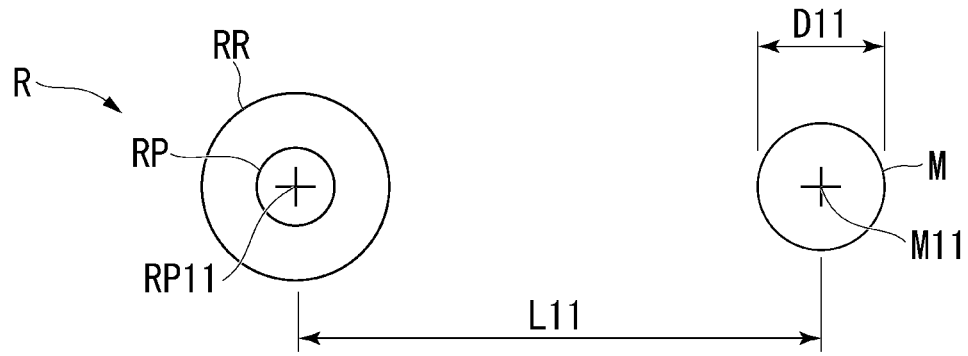
FIGS. 4A and 4B are diagrams for explaining a first example of analysis executed by the analysis unit of the eye movement analysis system of the first embodiment.
Figure 4B:
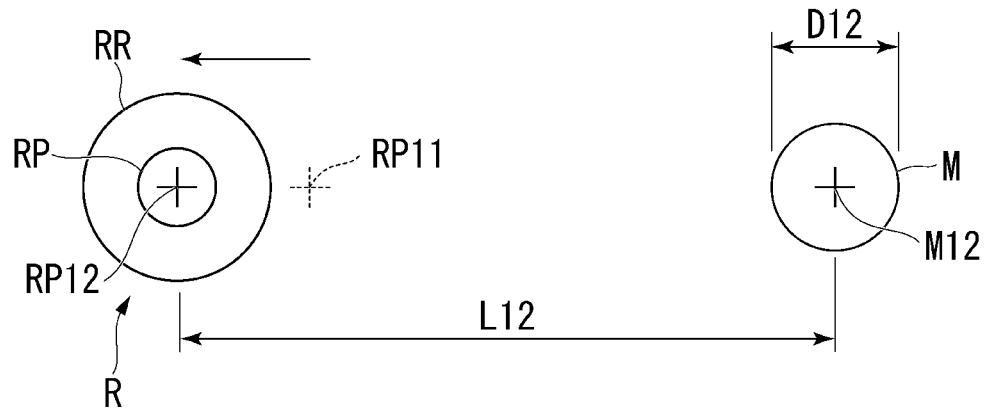

FIGS. 4A and 4B are diagrams for explaining a first example of analysis executed by the analysis unit 14 of the eye movement analysis system 1 of the first embodiment. In detail, FIG. 4A shows the relationship between the right eye R of the subject SB and the comparison target M on the moving image at time t11, among the moving images captured by the image-capturing unit 13. FIG. 4B shows the relationship between the right eye R of the subject SB and the comparison target M on the moving image at time t12 after the time t11, among the moving images captured by the image-capturing unit 13.

In the examples shown in FIGS. 4A and 4B, the acquisition unit 11 acquires the actual size D1 [mm] of the diameter of the comparison target M. The actual size D1 [mm] is, for example, 5 [mm] to 10 [mm].

Further, the diameter of the comparison target M on the moving image at the time t11 captured by the image-capturing unit 13 is D11 [pixel]. Further, the distance between the center (area centroid) RP11 of the pupil RP of the right eye R of the subject SB and the center (area centroid) M11 of the comparison target M on the moving image at the time t11 captured by the image-capturing unit 13 is L11 [pixel].

Further, the diameter of the comparison target M on the moving image at the time t12 captured by the image-capturing unit 13 is D12 [pixel]. Further, the distance between the center (area centroid) RP12 of the pupil RP of the right eye R of the subject SB and the center (area centroid) M12 of the comparison target M on the moving image at the time t12 captured by the image-capturing unit 13 is L12 [pixel].

In the examples shown in FIGS. 4A and 4B, the analysis unit 14 analyzes the movement of the eyeball of the right eye R of the subject SB, based on the actual size D1 [mm] of the diameter of the comparison target M acquired by the acquisition unit 11, the diameters D11 [pixel] and D12 [pixel] of the comparison target M on the moving image captured by the image-capturing unit 13, and the distances L11 [pixel] and L12 [pixel] between the centers (area centroids) RP11 and RP12 of the pupil RP of the right eye R of the subject SB and the centers (area centroid) M11 and M12 of the comparison target M on the moving image captured by the image-capturing unit 13.

Specifically, the analysis unit 14 calculates the actual distance (L11 [pixel]×D1 [mm]/D11 [pixel]) between the center (area centroid) RP11 of the pupil RP of the right eye R of the subject SB and the center (area centroid) M11 of the comparison target M at the time t11.

Further, the analysis unit 14 calculates the actual distance (L12 [pixel]×D1[mm]/D12 [pixel]) between the center (area centroid) RP12 of the pupil RP of the right eye R of the subject SB and the center (area centroid) M12 of the comparison target M at the time t12.

Further, the analysis unit 14 further calculates, for example, the actual movement amount (L12 [pixel]×D1 [mm]/D12 [pixel]−L11 [pixel]×D1[mm]/D11[pixel]) of the center (area centroid) of the pupil RP of the right eye R of the subject SB during the period from time t11 to time t12.

Further, the analysis unit 14 further calculates, for example, the actual movement speed (L12 [pixel]×D1[mm]/ D12[pixel]−L11 [pixel]×D1 [mm]/D11[pixel])/(t12−t11)) of the center (area centroid) of the pupil RP of the right eye R of the subject SB during the period from time t11 to time t12.

By performing such an operation, the analysis unit 14 analyzes the movement of the eyeball of the right eye R of the subject SB (for example, the movement amount (amplitude) and the movement speed of the eyeball of the right eye R due to nystagmus).

That is, in the examples shown in FIGS. 4A and 4B, the eye movement analysis system 1 of the first embodiment does not need to use the Purkinje image, does not need to perform calibration in advance, and can analyze the movement of the eyeball of the right eye R of the subject SB noninvasively and highly accurately, even when the distance between the image-capturing unit 13 and the subject SB changes (for example, when the face of the subject SB moves).

In the examples shown in FIGS. 4A and 4B, the center (area centroid) of the pupil RP is used as a point on the right eye R of the subject SB on the moving image captured by the image-capturing unit 13. However, in another example, as a point on the right eye R of the subject SB on the moving image captured by the image-capturing unit 13, a point other than the center (area centroid) of the pupil RP (for example, a characteristic point on the iris RR (not shown), characteristic points on conjunctival blood vessels (not shown), or the like) may be used.

In the examples shown in FIGS. 4A and 4B, the diameter of the comparison target M is used as the dimension of the comparison target M, but in other examples, the radius of the comparison target M may be used as the dimension of the comparison target M.

In the first example of the analysis executed by the analysis unit 14 of the eye movement analysis system 1 of the first embodiment, the analysis unit 14 analyzes the movement of the eyeball of the left eye L of the subject SB, in the same manner as the examples shown in FIGS. 4A and 4B.

Specifically, the analysis unit 14 analyzes the movement of the eyeball of the left eye L of the subject SB, based on the actual size of the diameter or radius of the comparison target M acquired by the acquisition unit 11, the diameter or radius of the comparison target M on the moving image captured by the image-capturing unit 13, and the distance between the point on the left eye L of the subject SB (for example, the center (area centroid) of the pupil of the left eye L) and the center (area centroid) of the comparison target M on the moving image captured by the image-capturing unit 13.

In the first example of the analysis executed by the analysis unit 14 of the eye movement analysis system 1 of the first embodiment, a high-speed infrared video camera (300 fps) is used as the image-capturing unit 13.

In another example, a camera other than the high-speed infrared video camera may be used as the image-capturing unit 13.

Further, in the first example of the analysis executed by the analysis unit 14 of the eye movement analysis system 1 of the first embodiment, the moving image captured by the high-speed infrared video camera as the image-capturing unit 13 is binarized by the analysis unit 14, for example, as shown in FIG. 2A.

In another example, the analysis unit 14 may perform another any image processing on the moving image captured by the image-capturing unit 13.

Figure 5A:
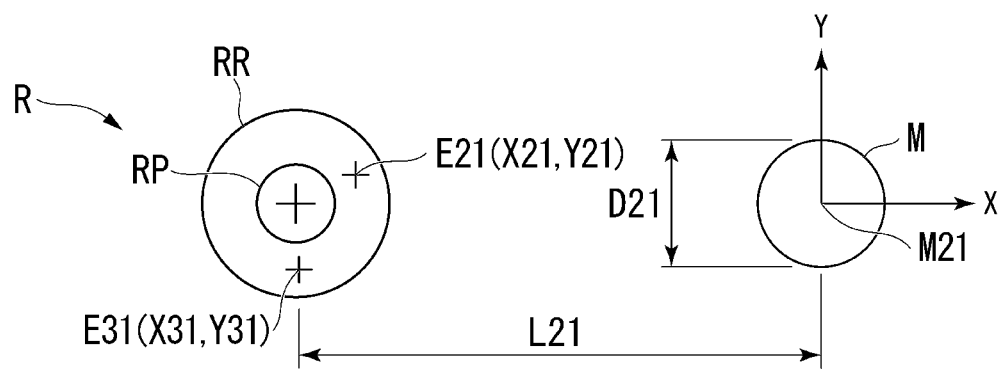
FIGS. 5A and 5B are diagrams for explaining a second example of analysis executed by the analysis unit of the eye movement analysis system of the first embodiment.
Figure 5B:
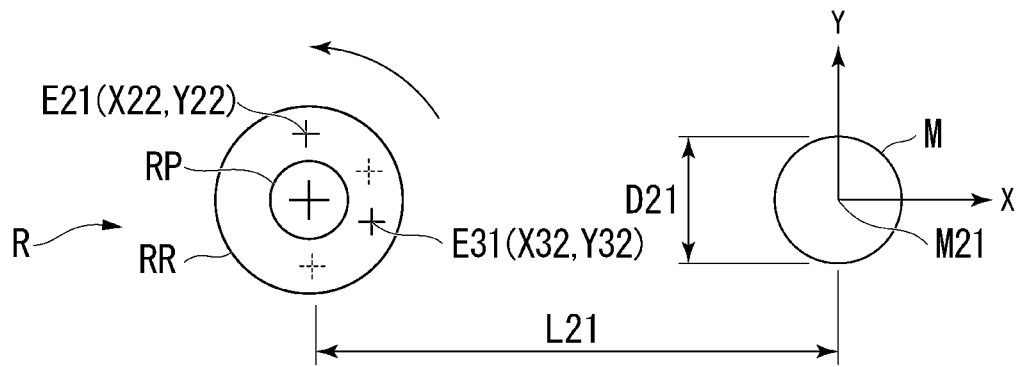

FIGS. 5A and 5B are diagrams for explaining a second example of analysis executed by the analysis unit 14 of the eye movement analysis system 1 of the first embodiment. In detail, FIG. 5A shows the relationship between the right eye R of the subject SB and the comparison target M on the moving image at time t21, among the moving images captured by the image-capturing unit 13. FIG. 5B shows the relationship between the right eye R of the subject SB and the comparison target M on the moving image at time t22 after the time t21, among the moving images captured by the image-capturing unit 13.

In the examples shown in FIGS. 5A and 5B, the acquisition unit 11 acquires the actual size D2 [mm] of the diameter of the comparison target M. The actual size D2 [mm] is, for example, 5 [mm] to 10 [mm].

Further, the diameter of the comparison target M on the moving image at the time t21 captured by the image-capturing unit 13 is D21 [pixel]. Further, the distance between the center (area centroid) of the pupil RP of the right eye R of the subject SB and the center (area centroid) M21 of the comparison target M on the moving image at the time t21 captured by the image-capturing unit 13 is L21 [pixel].

Further, the diameter of the comparison target M on the moving image at the time t22 captured by the image-capturing unit 13 is D21 [pixel] as at the time t21.

That is, in the examples shown in FIGS. 5A and 5B, the distance between the image-capturing unit 13 and the subject SB does not change between the time t21 and the time t22.

Further, the distance between the center (area centroid) of the pupil RP of the right eye R of the subject SB and the center (area centroid) M22 of the comparison target M on the moving image at the time t22 captured by the image-capturing unit 13 is L21 [pixel], as at the time t21.

That is, in the examples shown in FIGS. 5A and B, the distance between the center (area centroid) of the pupil RP of the right eye R of the subject SB and the centers (area centroids) M21 and M22 of the comparison target M does not change between time t21 and time t22.

In the examples shown in FIGS. 5A and 5B, in order to analyze the movement of the eyeball of the right eye R of the subject SB, the distance between the points E21 and E31 on the iris RR of the right eye R of the subject SB and the centers (area centroids) M21 and M22 of the comparison target M on the moving image captured by the image-capturing unit 13 is used.

That is, the analysis unit 14 analyzes the movement of the eyeball of the right eye R of the subject SB, based on the actual size D2 [mm] of the diameter of the comparison target M acquired by the acquisition unit 11, the diameter D21 [pixel] of the comparison target M on the moving image captured by the image-capturing unit 13, and the distance between the points E21 and E31 on the iris RR of the right eye R of the subject SB and the centers (area centroids) M21 and M22 of the comparison target M on the moving image captured by the image-capturing unit 13.

Specifically, in the examples shown in FIGS. 5A and 5B, the two-dimensional coordinates of the center (area centroid) M21 of the comparison target M at the time t21 on the moving image captured by the image-capturing unit 13 is set to the origin (0,0). Further, the two-dimensional coordinates of the point E21 on the iris RR of the right eye R of the subject SB at the time t21 on the moving image captured by the image-capturing unit 13 are (X21, Y21), and the two-dimensional coordinates of the point E31 on which are (X31, Y31).

Next, the two-dimensional coordinates of the center (area centroid) M22 of the comparison target M at the time t22 on the moving image captured by the image-capturing unit 13 is set to the origin (0,0). Further, the two-dimensional coordinates of the point E21 on the iris RR of the right eye R of the subject SB at the time t22 on the moving image captured by the image-capturing unit 13 are (X22, Y22)(≠(X21, Y21)), and the two-dimensional coordinates of the point E31 on which are (X32, Y32)(≠(X31, Y31)).

That is, in the examples shown in FIGS. 5A and 5B, based on the diameter D21 [pixel] of the comparison target M at the times t21 and t22 on the moving image captured by the image-capturing unit 13, the two-dimensional coordinates (X21, Y21) of the point E21 and the two-dimensional coordinates (X31, Y31) of the point E31 on the iris RR of the right eye R of the subject SB at the time t21 on the moving image captured by the image-capturing unit 13, the two-dimensional coordinates (X22, Y22) of the point E21 and the two-dimensional coordinates (X32, Y32) of the point E31 on the iris RR of the right eye R of the subject SB at the time t22 on the moving image captured by the image-capturing unit 13, the analysis unit 14 can analyze that the eyeball of the right eye R of the subject SB has rotated counterclockwise as shown by the arrow in FIG. 5B, although the distance between the center (area centroid) of the pupil RP of the right eye R of the subject SB and the centers (area centroids) M21 and M22 of the comparison target M does not change between time t21 and time t22.

In the examples shown in FIGS. 5A and 5B, the distance between the image-capturing unit 13 and the subject SB does not change between the time t21 and the time t22, but even when the distance between the image-capturing unit 13 and the subject SB changes between the time t21 and the time t22, by using the information of the diameter (unit is [pixel]) of the comparison target M on the moving image at time t21 and the information of the diameter (unit is [pixel]) of the comparison target M on the moving image at time t22, it can be analyzed that the eyeball of the right eye R of the subject SB has rotated, as in the examples shown in FIGS. 5A and 5B.

In the examples shown in FIGS. 5A and 5B, the diameter of the comparison target M is used as the dimension of the comparison target M, but in other examples, the radius of the comparison target M may be used as the dimension of the comparison target M.

In the second example of the analysis executed by the analysis unit 14 of the eye movement analysis system 1 of the first embodiment, the analysis unit 14 analyzes the movement of the eyeball of the left eye L of the subject SB, in the same manner as the examples shown in FIGS. 5A and 5B.

Specifically, the analysis unit 14 analyzes the movement of the eyeball of the left eye L of the subject SB, based on the actual size of the diameter or radius of the comparison target M acquired by the acquisition unit 11, the diameter or radius of the comparison target M on the moving image captured by the image-capturing unit 13, and the distance between the point on the iris of the left eye L of the subject SB and the center (area centroid) of the comparison target M on the moving image captured by the image-capturing unit 13.

That is, in the second example of the analysis executed by the analysis unit 14 of the eye movement analysis system 1 of the first embodiment, the analysis unit 14 can analyze that the eyeball of the left eye L of the subject SB has rotated, based on the diameter (unit is [pixel]) of the comparison target M at different time points on the moving image captured by the image-capturing unit 13, and the two-dimensional coordinates of two points on the iris of the left eye L of the subject SB at the different time points on the moving image captured by the image-capturing unit 13.

Figure 6A:
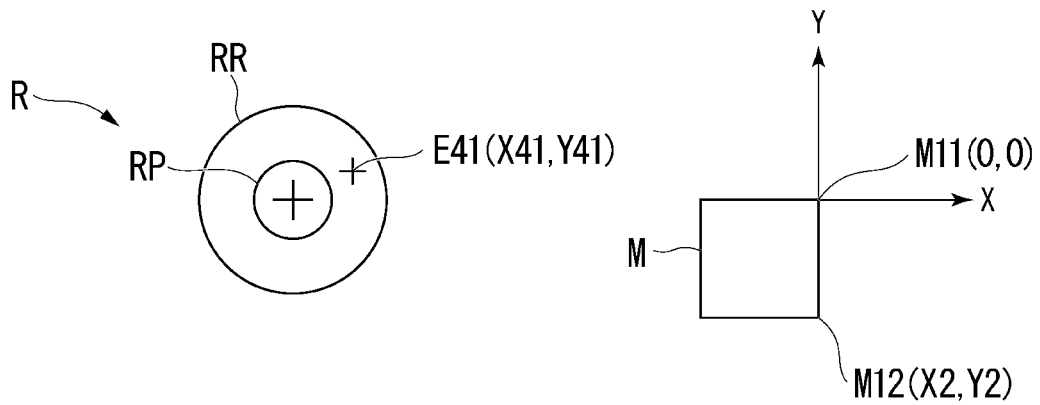
FIGS. 6A and 6B are diagrams for explaining a third example of analysis executed by the analysis unit of the eye movement analysis system of the first embodiment.
Figure 6B:
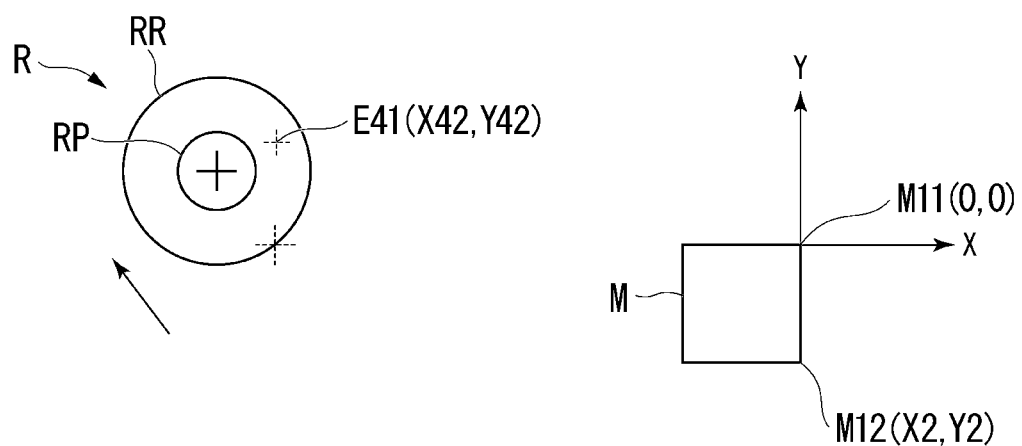

FIGS. 6A and 6B are diagrams for explaining a third example of analysis executed by the analysis unit 14 of the eye movement analysis system 1 of the first embodiment. In detail, FIG. 6A shows the relationship between the right eye R of the subject SB and the comparison target M on the moving image at time t31, among the moving images captured by the image-capturing unit 13. FIG. 6B shows the relationship between the right eye R of the subject SB and the comparison target M on the moving image at time t32 after the time t31, among the moving images captured by the image-capturing unit 13.

In the examples shown in FIGS. 6A and 6B, the shape of the comparison target M is polygonal (for example, rectangular). The acquisition unit 11 acquires the actual size S1 [mm] of the distance between the vertex M11 and the vertex M12 of the comparison target M. The actual size S1 [mm] is, for example, 5 [mm] to 10 [mm].

Further, the two-dimensional coordinates of the vertex M11 of the comparison target M at the time t31 on the moving image captured by the image-capturing unit 13 are set to the origin (0,0). Further, the two-dimensional coordinates of the vertex M12 of the comparison target M at the time t31 on the moving image captured by the image-capturing unit 13 are (X2, Y2). Further, the two-dimensional coordinates of the point E41 on the iris RR of the right eye R of the subject SB at the time t31 on the moving image captured by the image-capturing unit 13 are (X41, Y41).

Next, the two-dimensional coordinates of the vertex M11 of the comparison target M at the time t32 on the moving image captured by the image-capturing unit 13 are set to the origin (0, 0). Further, the two-dimensional coordinates of the vertex M12 of the comparison target M at the time t32 on the moving image captured by the image-capturing unit 13 are (X2, Y2) as at the time t31.

That is, in the examples shown in FIGS. 6A and 6B, the distance between the image-capturing unit 13 and the subject SB does not change between the time t31 and the time t32.

Further, the two-dimensional coordinates of the point E41 on the iris RR of the right eye R of the subject SB at the time t32 on the moving image captured by the image-capturing unit 13 are (X42, Y42).

In the examples shown in FIGS. 6A and 6B, in order to analyze the movement of the eyeball of the right eye R of the subject SB, the actual size S1 [mm] of the distance between the vertex M11 and the vertex M12 of the comparison target M acquired by the acquisition unit 11, the dimension of the comparison target M on the moving image captured by the image-capturing unit 13 (specifically, the dimension (distance) between the vertex M11 and the vertex M12 obtained from the two-dimensional coordinates (0,0) of the vertex M11 and the two-dimensional coordinates (X2, Y2) of the vertex M12), and the positional relationship between the point E41 on the iris RR of the right eye R of the subject SB and the comparison target M on the moving image captured by the image-capturing unit 13 are used.

That is, the analysis unit 14 analyzes the movement of the eyeball of the right eye R of the subject SB, based on the actual size S1 [mm] of the distance between the vertex M11 and the vertex M12 of the comparison target M acquired by the acquisition unit 11, the dimension of the comparison target M on the moving image captured by the image-capturing unit 13 (specifically, the dimension (distance) between the vertex M11 and the vertex M12 obtained from the two-dimensional coordinates (0,0) of the vertex M11 and the two-dimensional coordinates (X2, Y2) of the vertex M12), and the positional relationship between the point E41 on the iris RR of the right eye R of the subject SB and the comparison target M on the moving image captured by the image-capturing unit 13.

Specifically, in the examples shown in FIGS. 6A and 6B, the two-dimensional coordinates of the point E41 on the iris RR of the right eye R of the subject SB at the time t31 on the moving image captured by the image-capturing unit 13 are (X41, Y41).

Further, the two-dimensional coordinates of the point E41 on the iris RR of the right eye R of the subject SB at the time t32 on the moving image captured by the image-capturing unit 13 are (X42, Y42)($\neq$(X41, Y41)).

That is, in the examples shown in FIGS. 6A and 6B, based on the relative coordinates (X2, Y2) of the vertex M12 relative to the vertex M11 of the comparison target M at the times t31 and t32 on the moving image captured by the image-capturing unit 13, the two-dimensional coordinates (X41, Y41) of the point E41 on the iris RR of the right eye R of the subject SB at the time t31 on the moving image captured by the image-capturing unit 13, and the two-dimensional coordinates (X42, Y42) of the point E41 on the iris RR of the right eye R of the subject SB at the time t32 on the moving image captured by the image-capturing unit 13, the analysis unit 14 can analyze, between the time t31 and time t32, not only that the distance between the eyeball of the right eye R of the subject SB and the comparison target M has changed (increased), but also that as shown by the arrow in FIG. 6B, the eyeball of the right eye R of the subject SB has moved toward the upper left of FIG. 6B (that is, the direction of movement of the eyeball).

That is, in the examples shown in FIGS. 6A and 6B, the analysis unit 14 analyzes the movement of the eyeball of the right eye R of the subject SB, based on the actual size S1 [mm] of the distance between the vertex M11 and the vertex M12 of the polygon of the comparison target M acquired by the acquisition unit 11, the distance $((X2^2+Y2^2)^{1/2}$[pixel]) between the vertex M11 and the vertex M12 of the comparison target M on the moving image captured by the image-capturing unit 13, and the positional relationship between the point E41 on the iris RR of the right eye R of the subject SB and the vertices M11 and M12 of the polygon of the comparison target M at the time t31 and time t32 on the moving image captured by the image-capturing unit 13.

In the examples shown in FIGS. 6A and 6B, the distance between the image-capturing unit 13 and the subject SB does not change between the time t31 and the time t32, but when the distance between the image-capturing unit 13 and the subject SB changes between the time t31 and the time t32, the direction of the movement of the eyeball of the right eye R of the subject SB can be analyzed by using the information of the two-dimensional coordinates of the vertex M12 of the comparison target M on the moving image at time t31 and the information of the two-dimensional coordinates of the vertex M12 of the comparison target M on the moving image at time t32, in the same manner as the example shown in FIGS. 6A and 6B.

In the third example of the analysis executed by the analysis unit 14 of the eye movement analysis system 1 of the first embodiment, the analysis unit 14 analyzes the movement of the eyeball of the left eye L of the subject SB, in the same manner as the examples shown in FIGS. 6A and 6B.

Specifically, the analysis unit 14 analyzes the movement of the eyeball of the left eye L of the subject SB, based on the actual size S1 [mm] of the distance between the vertex M11 and the vertex M12 of the polygon of the comparison target M acquired by the acquisition unit 11, the distance (unit is [pixel]) between the vertex M11 and the vertex M12 of the comparison target M on the moving image captured by the image-capturing unit 13, and the positional relationship between the point (not shown) on the iris of the left eye L of the subject SB at the time t31 and time t32 and the vertices M11 and M12 of the polygon of the comparison target M on the moving image captured by the image-capturing unit 13.

That is, in the third example of the analysis executed by the analysis unit 14 of the eye movement analysis system 1 of the first embodiment, the analysis unit 14 can analyze the direction of movement of the eyeball of the left eye L of the subject SB, based on the distance (unit is [pixel]) between the vertex M11 and the vertex M12 of the comparison target M at different time points on the moving image captured by the image-capturing unit 13, and the two-dimensional coordinates of the point on the iris of the left eye L of the subject SB at different time points on the moving image captured by the image-capturing unit 13.

Figure 7A:
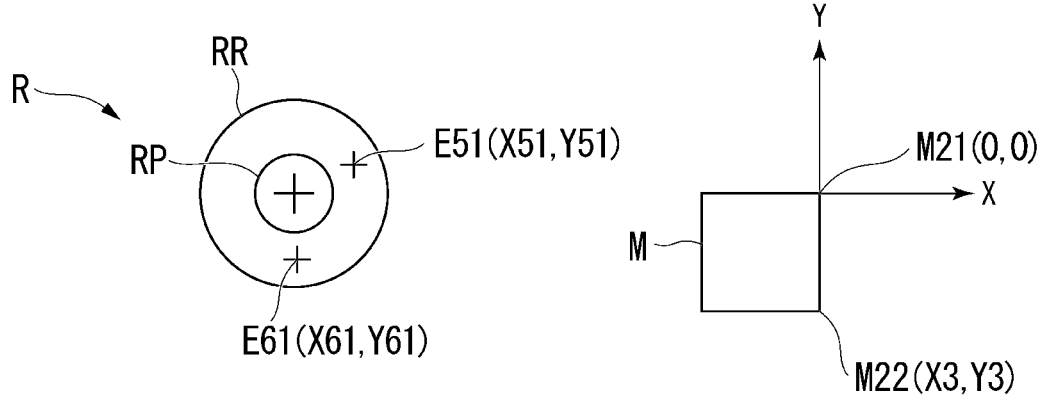
FIGS. 7A and 7B are diagrams for explaining a fourth example of analysis executed by the analysis unit of the eye movement analysis system of the first embodiment.
Figure 7B:
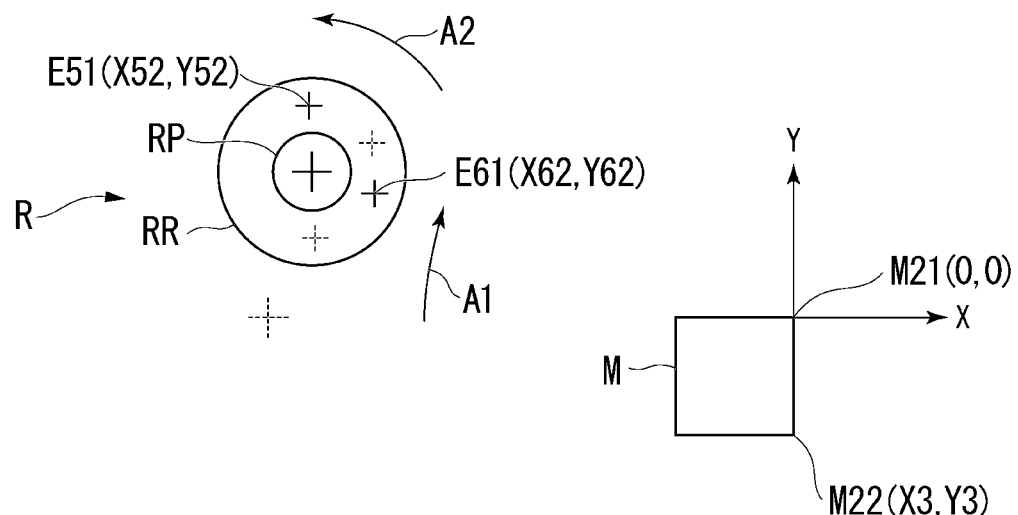

FIGS. 7A and 7B are diagrams for explaining a fourth example of analysis executed by the analysis unit 14 of the eye movement analysis system 1 of the first embodiment. In detail, FIG. 7A shows the relationship between the right eye R of the subject SB and the comparison target M on the moving image at time t41, among the moving images captured by the image-capturing unit 13. FIG. 7B shows the relationship between the right eye R of the subject SB and the comparison target M on the moving image at time t42 after the time t41, among the moving images captured by the image-capturing unit 13.

In the examples shown in FIGS. 7A and 7B, the shape of the comparison target M is polygonal (for example, rectangular). The acquisition unit 11 acquires the actual size S1 [mm] of the distance between the vertex M21 and the vertex M22, connecting the vertex M21 and the vertex M22 of the comparison target M. The actual size S1 [mm] is, for example, 5 [mm] to 10 [mm].

Further, the two-dimensional coordinates of the vertex M21 of the comparison target M at the time t41 on the moving image captured by the image-capturing unit 13 are set to the origin (0,0). Further, the two-dimensional coordinates of the vertex M22 of the comparison target M at the time t41 on the moving image captured by the image-capturing unit 13 are (X3, Y3). Further, the two-dimensional coordinates of the point E51 on the iris RR of the right eye R of the subject SB at the time t41 on the moving image captured by the image-capturing unit 13 are (X51, Y51), and the two-dimensional coordinates of the point E61 on which are (X61, Y61).

Next, the two-dimensional coordinates of the vertex M21 of the comparison target M at the time t42 on the moving image captured by the image-capturing unit 13 are set to the origin (0, 0). Further, the two-dimensional coordinates of the vertex M22 of the comparison target M at the time t42 on the moving image captured by the image-capturing unit 13 are (X3, Y3) as at the time t41.

That is, in the examples shown in FIGS. 7A and 7B, the distance between the image-capturing unit 13 and the subject SB does not change between the time t41 and the time t42.

Further, the two-dimensional coordinates of the point E51 on the iris RR of the right eye R of the subject SB at the time t42 on the moving image captured by the image-capturing unit 13 are (X52, Y52), and the two-dimensional coordinates of the point E61 on which are (X62, Y62).

In the examples shown in FIGS. 7A and 7B, in order to analyze the movement of the eyeball of the right eye R of the subject SB, the actual size S1 [mm] of the distance between the vertex M21 and the vertex M22 of the comparison target M acquired by the acquisition unit 11, the dimension of the comparison target M on the moving image captured by the image-capturing unit 13 (specifically, the dimension (distance) between the vertex M21 and the vertex M22 obtained from the two-dimensional coordinates (0,0) of the vertex M21 and the two-dimensional coordinates (X3, Y3) of the vertex M22), and the positional relationship between the points E51 and E61 on the iris RR of the right eye R of the subject SB and the comparison target M on the moving image captured by the image-capturing unit 13 are used.

That is, the analysis unit 14 analyzes the movement of the eyeball of the right eye R of the subject SB, based on the actual size S1 [mm] of the side length of the comparison target M acquired by the acquisition unit 11, the dimension of the comparison target M on the moving image captured by the image-capturing unit 13 (specifically, the dimension (distance) between the vertex M21 and the vertex M22 obtained from the two-dimensional coordinates (0,0) of the vertex M21 and the two-dimensional coordinates (X3, Y3) of the vertex M22), and the positional relationship between the points E51, E61 on the iris RR of the right eye R of the subject SB and the comparison target M on the moving image captured by the image-capturing unit 13.

Specifically, in the examples shown in FIGS. 7A and 7B, the two-dimensional coordinates of the point E51 on the iris RR of the right eye R of the subject SB at the time t41 on the moving image captured by the image-capturing unit 13 are (X51, Y51).

Further, the two-dimensional coordinates of the point E51 on the iris RR of the right eye R of the subject SB at the time t42 on the moving image captured by the image-capturing unit 13 are (X52, Y52) (≠(X51, Y51)).

Further, the two-dimensional coordinates of the point E61 on the iris RR of the right eye R of the subject SB at the time t41 on the moving image captured by the image-capturing unit 13 are (X61, Y61).

Further, the two-dimensional coordinates of the point E61 on the iris RR of the right eye R of the subject SB at the time t42 on the moving image captured by the image-capturing unit 13 are (X62, Y62) (≠(X61, Y61)).

That is, in the examples shown in FIGS. 7A and 7B, based on the relative coordinates (X3, Y3) of the vertex M22 relative to the vertex M21 of the comparison target M at the times t41 and t42 on the moving image captured by the image-capturing unit 13, the two-dimensional coordinates (X51, Y51) of the point E51 on the iris RR of the right eye R of the subject SB at the time t41 on the moving image captured by the image-capturing unit 13, the two-dimensional coordinates (X52, Y52) of the point E51 on the iris RR of the right eye R of the subject SB at the time t42 on the moving image captured by the image-capturing unit 13, the two-dimensional coordinates (X61, Y61) of the point E61 on the iris RR of the right eye R of the subject SB at the time t41 on the moving image captured by the image-capturing unit 13, and the two-dimensional coordinates (X62, Y62) of the point E61 on the iris RR of the right eye R of the subject SB at the time t42 on the moving image captured by the image-capturing unit 13, the analysis unit 14 can analyze that, between the time 41 and time 42, the distance between the eyeball of the right eye R of the subject SB and the comparison target M has not changed, but as shown by the arrow A1 in FIG. 7B, the eyeball of the right eye R of the subject SB has swirled clockwise around the comparison target M (that is, the direction of movement of the eyeball), and as shown by the arrow A2 in FIG. 7B, the eyeball of the right eye R of the subject SB has rotated counterclockwise.

That is, in the examples shown in FIGS. 7A and B, the analysis unit 14 analyzes the movement of the eyeball of the right eye R of the subject SB, based on the actual size S1 [mm] of the distance between the vertex M21 and the vertex M22 of the polygon of the comparison target M acquired by the acquisition unit 11, the distance $((X3^2+Y3^2)^{1/2}$ [pixel]) between the vertex M21 and the vertex M22 of the comparison target M on the moving image captured by the image-capturing unit 13, the positional relationship between the point E51 on the iris RR of the right eye R of the subject SB and the vertices M21 and M22 of the polygon of the comparison target M at the time t41 and time t42 on the moving image captured by the image-capturing unit 13, and the positional relationship between the point E61 on the iris RR of the right eye R of the subject SB and the vertices M21 and M22 of the polygon of the comparison target M at the time t41 and time t42 on the moving image captured by the image-capturing unit 13.

In the examples shown in FIGS. 7A and 7B, the distance between the image-capturing unit 13 and the subject SB does not change between the time t41 and the time t42, but even when the distance between the image-capturing unit 13 and the subject SB changes between the time t41 and the time t42, the direction of the movement of the eyeball of the right eye R of the subject SB and the rotation of the eyeball can be analyzed by using the information of the two-dimensional coordinates of the vertex M22 of the comparison target M on the moving image at time t41 and the information of the two-dimensional coordinates of the vertex M22 of the comparison target M on the moving image at time t42, as in the example shown in FIGS. 7A and 7B.

In the fourth example of the analysis executed by the analysis unit 14 of the eye movement analysis system 1 of the first embodiment, the analysis unit 14 analyzes the movement of the eyeball of the left eye L of the subject SB, in the same manner as the examples shown in FIGS. 7A and 7B.

Specifically, the analysis unit 14 analyzes the movement of the eyeball of the left eye L of the subject SB, based on the actual size S1 [mm] of the distance between the vertex M21 and the vertex M22 of the polygon of the comparison target M acquired by the acquisition unit 11, the distance (unit is [pixel]) between the vertex M21 and the vertex M22 of the comparison target M on the moving image captured by the image-capturing unit 13, and the positional relationship between two points (not shown) on the iris of the left eye L of the subject SB and the vertices M21 and M22 of the polygon of the comparison target M at the time t41 and time t42 on the moving image captured by the image-capturing unit 13.

That is, in the fourth example of the analysis executed by the analysis unit 14 of the eye movement analysis system 1 of the first embodiment, the analysis unit 14 can analyze the direction of movement of the eyeball and the rotation of the eyeball of the left eye L of the subject SB, based on the distance (unit is [pixel]) between two vertices M21 and M22 of the comparison target M at different time points on the moving image captured by the image-capturing unit 13, and the two-dimensional coordinates of the two points on the iris of the left eye L of the subject SB at different time points on the moving image captured by the image-capturing unit 13.

As described above, in the first to fourth examples of the analysis executed by the analysis unit 14 of the eye movement analysis system 1 of the first embodiment, the acquisition unit 11 acquires information of the actual size D1 [mm] of the diameter of the comparison target M, but in the fifth example of the analysis executed by the analysis unit 14 of the eye movement analysis system 1 of the first embodiment, the acquisition unit 11 may not acquire information of the actual size D1 [mm] of the diameter of the comparison target M.

In the fifth example of the analysis executed by the analysis unit 14 of the eye movement analysis system 1 of the first embodiment, the movement of the eyeball of the right eye R of the subject SB (for example, whether or not the movement has been done, the direction of movement, or the like) is analyzed, by comparing the distance between a plurality of points on the comparison target M on the moving image captured by the image-capturing unit 13, and the positional relationship between the comparison target M and the right eye R of the subject SB on the moving image captured by the image-capturing unit 13 at a plurality of time points.

Further, in the fifth example of the analysis executed by the analysis unit 14 of the eye movement analysis system 1 of the first embodiment, the movement of the eyeball of the left eye L of the subject SB (for example, whether or not the movement has been done, the direction of movement, or the like) is analyzed, by comparing the distance between a plurality of points on the comparison target M on the moving image captured by the image-capturing unit 13, and the positional relationship between the comparison target M and the left eye L of the subject SB on the moving image captured by the image-capturing unit 13 at a plurality of time points.

That is, in the fifth example of the analysis performed by the analysis unit 14 of the eye movement analysis system 1 of the first embodiment, it is possible to obtain the time waveforms of the eye movements of the right eye R and the left eye L of the subject SB, and it can be used for simple screening.

In a fifth example of the analysis performed by the analysis unit 14 of the eye movement analysis system 1 of the first embodiment, the morphological features on the surface of the face of the subject SB (for example, areas where the position changes little due to the change in the facial expression of the subject SB, such as moles, ears, nose, outer corners of eyes, and inner corners of eyes) are used as the comparison target M.

Specifically, the analysis unit 14 analyzes the movement of the eyeball of the right eye R of the subject SB, based on the relationship between the right eye R of the subject SB and the two points on the morphological feature (comparison target M) on the moving image captured by the image-capturing unit 13. Specifically, the analysis unit 14 analyzes the movement of the eyeball of the right eye R of the subject SB, based on the distance between the two points on the comparison target M (morphological feature) on the moving image captured by the image-capturing unit 13, and the positional relationship between the point on the right eye R of the subject SB and the two points on the comparison target M (morphological feature) on the moving image captured by the image-capturing unit 13.

Further, the analysis unit 14 analyzes the movement of the eyeball of the left eye L of the subject SB, based on the relationship between the left eye L of the subject SB and the two points on the morphological feature (comparison target M) on the moving image captured by the image-capturing unit 13. Specifically, the analysis unit 14 analyzes the movement of the eyeball of the left eye L of the subject SB, based on the distance between the two points on the comparison target M (morphological feature) on the moving image captured by the image-capturing unit 13, and the positional relationship between the point on the left eye L of the subject SB and the two points on the comparison target M (morphological feature) on the moving image captured by the image-capturing unit 13.

When the morphological feature on the surface of the face of the subject SB is used as the comparison target M, the acquisition unit 11 may acquire the distance (actual size) between the two points on the morphological feature (comparison target M). In this example, the distance (actual size) between two points on the morphological feature (comparison target M) is obtained by measurement with a caliper, for example. In yet another example, by using the autofocus function of the image-capturing unit 13, the distance (actual size) between the two points on the morphological feature (comparison target M) may be estimated, based on the distance between the image-capturing unit 13 and the subject SB.

FIGS. 8A-8H are diagrams for explaining another example of the comparison target M.

Figure 8A:
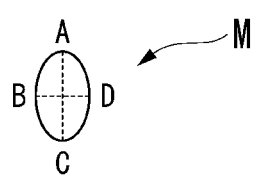
FIGS. 8A-8H are diagrams for explaining another example of a comparison target.

In the example shown in FIG. 8A, the comparison target M is an elliptical sticker. The information of the comparison target M (elliptical sticker) acquired by the acquisition unit 11 includes the actual size of the distance between two points on the comparison target M (for example, one of the actual size of the major axis AC, the actual size of the semimajor axis (½ of the major axis AC), the actual size of the minor axis BD, and the actual size of semiminor axis (½ of minor axis BD).

In the example shown in FIG. 8A, in order to analyze the movement of the eyeball of the right eye R of the subject SB, the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13 are used.

That is, the analysis unit 14 analyzes the movement of the eyeball of the right eye R of the subject SB, based on the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13.

Similarly, the analysis unit 14 analyzes the movement of the eyeball of the left eye L of the subject SB, based on the actual size of the distance between the two points on the comparison target M acquired by the acquisition unit 11, the distance between the two points on the comparison target M on the moving image captured by the image-capturing unit 13, and the positional relationship between the point on the left eye L of the subject SB and the two points on the comparison target M on the moving image captured by the image-capturing unit 13.

In the example in which the acquisition unit 11 does not acquire the actual size of the distance between the two points on the comparison target M, the analysis unit 14 analyzes the movement of the eyeball of the right eye R of the subject SB, based on the distance between the two points on the comparison target M on the moving image captured by the image-capturing unit 13, and the positional relationship between the point on the right eye R of the subject SB and the two points on the comparison target M on the moving image captured by the image-capturing unit 13.

Further, the analysis unit 14 analyzes the movement of the eyeball of the left eye L of the subject SB, based on the distance between the two points on the comparison target M on the moving image captured by the image-capturing unit 13, and the positional relationship between the point on the left eye L of the subject SB and the two points on the comparison target M on the moving image captured by the image-capturing unit 13.

For example, in the example in which the comparison target M is attached to the subject SB such that the major axis AC shown in FIG. 8A is included in the vertical line (that is, the minor axis BD is included in the horizontal line), the analysis unit 14 can determine whether or not the inclination of the face of the subject SB has changed, based on the orientation of the comparison target M (oval sticker) on the moving image captured by the image-capturing unit 13. Specifically, the analysis unit 14 can determine the inclination of the face of the subject SB, based on the positional relationship between points A and C (or positional relationship between points B and D) of the comparison target M (elliptical sticker) on the moving image captured by the image-capturing unit 13.

That is, in this example, an elliptical sticker as the comparison target M is attached to the subject SB such that the inclination of the face of the subject SB can be determined from the moving image captured by the image-capturing unit 13.

Further, in this example, the analysis unit 14 determines the inclination of the face of the subject SB from the moving image captured by the image-capturing unit 13 by using two points on the elliptical sticker.

Figure 8B:
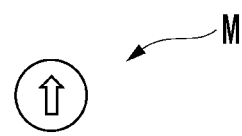

In the example shown in FIG. 8B, the comparison target M is a sticker having an arrow symbol indicating the top and bottom. The information of the comparison target M (sticker having the arrow symbol) acquired by the acquisition unit 11 includes the actual size of the distance between the two points on the arrow symbol of the comparison target M.

In the example shown in FIG. 8B, in order to analyze the movement of the eyeball of the right eye R of the subject SB, the actual size of the distance between the two points on the arrow symbol of the comparison target M acquired by the acquisition unit 11, the distance between the two points on the arrow symbol of the comparison target M on the moving image captured by the image-capturing unit 13, and the positional relationship between the point on the right eye R of the subject SB and the two points on the arrow symbol of the comparison target M on the moving image captured by the image-capturing unit 13 are used.

That is, the analysis unit 14 analyzes the movement of the eyeball of the right eye R of the subject SB, based on the actual size of the distance between the two points on the arrow symbol of the comparison target M acquired by the acquisition unit 11, the distance between the two points on the arrow symbol of the comparison target M on the moving image captured by the image-capturing unit 13, and the positional relationship between the point on the right eye R of the subject SB and the two points on the arrow symbol of the comparison target M on the moving image captured by the image-capturing unit 13.

Similarly, the analysis unit 14 analyzes the movement of the eyeball of the left eye L of the subject SB, based on the actual size of the distance between the two points on the arrow symbol of the comparison target M acquired by the acquisition unit 11, the distance between the two points on the arrow symbol of the comparison target M on the moving image captured by the image-capturing unit 13, and the positional relationship between the point on the left eye L of the subject SB and the two points on the arrow symbol of the comparison target M on the moving image captured by the image-capturing unit 13.

In the example in which the acquisition unit 11 does not acquire the actual size of the distance between the two points on the arrow symbol of the comparison target M, the analysis unit 14 analyzes the movement of the eyeball of the right eye R of the subject SB, based on the distance between the two points on the arrow symbol of the comparison target M on the moving image captured by the image-capturing unit 13, and the positional relationship between the point on the right eye R of the subject SB and the two points on the arrow symbol of the comparison target M on the moving image captured by the image-capturing unit 13.

Further, the analysis unit 14 analyzes the movement of the eyeball of the left eye L of the subject SB, based on the distance between the two points on the arrow symbol of the comparison target M on the moving image captured by the image-capturing unit 13, and the positional relationship between the point on the left eye L of the subject SB and the two points on the arrow symbol of the comparison target M on the moving image captured by the image-capturing unit 13.

For example, in the example in which the comparison target M is attached to the subject SB such that the arrow symbol shown in FIG. 8B is located on the vertical line (that is, the comparison target M is arranged as shown in FIG. 8B), the analysis unit 14 can determine whether or not the inclination of the face of the subject SB has changed, based on the orientation of the comparison target M (the sticker having the arrow symbol) on the moving image captured by the image-capturing unit 13. Specifically, the analysis unit 14 can determine the inclination of the face of the subject SB, based on the orientation of the arrow symbol of the comparison target M on the moving image captured by the image-capturing unit 13.

That is, in this example, a sticker having an arrow symbol as the comparison target M is attached to the subject SB such that the inclination of the face of the subject SB can be determined from the moving image captured by the image-capturing unit 13.

Further, in this example, the analysis unit 14 determines the inclination of the face of the subject SB from the moving image captured by the image-capturing unit 13, by using two points on the arrow symbol of the sticker.

Figure 8C:
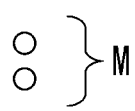

In the example shown in FIG. 8C, the comparison target M is composed of two stickers. The information of the comparison target M acquired by the acquisition unit 11 includes the actual size (for example, measured by a caliper) of the interval between the two stickers constituting the comparison target M.

In the example shown in FIG. 8C, in order to analyze the movement of the eyeball of the right eye R of the subject SB, the actual size of the interval between the two stickers constituting the comparison target M acquired by the acquisition unit 11, the interval between the two stickers constituting the comparison target M on the moving image captured by the image-capturing unit 13, and the positional relationship between the point on the right eye R of the subject SB and the two stickers constituting the comparison target M on the moving image captured by the image-capturing unit 13 are used.

That is, the analysis unit 14 analyzes the movement of the eyeball of the right eye R of the subject SB, based on the actual size of the interval between the two stickers constituting the comparison target M acquired by the acquisition unit 11, the interval between the two stickers constituting the comparison target M on the moving image captured by the image-capturing unit 13, and the positional relationship between the point on the right eye R of the subject SB and the two stickers constituting the comparison target M on the moving image captured by the image-capturing unit 13.

Similarly, the analysis unit 14 analyzes the movement of the eyeball of the left eye L of the subject SB, based on the actual size of the interval between the two stickers constituting the comparison target M acquired by the acquisition unit 11, the interval between the two stickers constituting the comparison target M on the moving image captured by the image-capturing unit 13, and the positional relationship between the point on the left eye L of the subject SB and the two stickers constituting the comparison target M on the moving image captured by the image-capturing unit 13.

In the example in which the acquisition unit 11 does not acquire the actual size of the interval between the two stickers constituting the comparison target M, the analysis unit 14 analyzes the movement of the eyeball of the right eye R of the subject SB, based on the interval between the two stickers constituting the comparison target M on the moving image captured by the image-capturing unit 13, and the positional relationship between the point on the right eye R of the subject SB and the two stickers constituting the comparison target M on the moving image captured by the image-capturing unit 13.

Further, the analysis unit 14 analyzes the movement of the eyeball of the left eye L of the subject SB, based on the interval between the two stickers constituting the comparison target M on the moving image captured by the image-capturing unit 13, and the positional relationship between the point on the left eye L of the subject SB and the two stickers constituting the comparison target M on the moving image captured by the image-capturing unit 13.

For example, in the example in which the two stickers constituting the comparison target M are attached to the subject SB such that the two stickers shown in FIG. 8C are located on the vertical line (that is, the two stickers are arranged as shown in FIG. 8C), the analysis unit 14 can determine whether or not the inclination of the face of the subject SB has changed, based on the arrangement (orientation) of the two stickers on the moving image captured by the image-capturing unit 13. Specifically, the analysis unit 14 can determine the inclination of the face of the subject SB, based on the arrangement (orientation) of the two stickers on the moving image captured by the image-capturing unit 13.

That is, in this example, the two stickers constituting the comparison target M are attached to the subject SB such that the inclination of the face of the subject SB can be determined from the moving image captured by the image-capturing unit 13.

Further, in this example, the analysis unit 14 determines the inclination of the face of the subject SB from the moving image captured by the image-capturing unit 13 by using, for example, the center point of each of the two stickers.

Figure 8D:
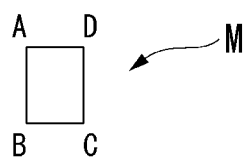

In the example shown in FIG. 8D, the comparison target M is a rectangular sticker. The information of the comparison target M (rectangular sticker) acquired by the acquisition unit 11 includes the actual size of the distance between two points (two vertices of a rectangle) on the comparison target M (for example, the actual size of the side AB, the actual size of the side DC, the actual size of the side AD, the actual size of the side BC, and the like).

In the example shown in FIG. 8D, in order to analyze the movement of the eyeball of the right eye R of the subject SB, the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13 are used.

That is, the analysis unit 14 analyzes the movement of the eyeball of the right eye R of the subject SB, based on the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13.

Similarly, the analysis unit 14 analyzes the movement of the eyeball of the left eye L of the subject SB, based on the actual size of the distance between the two points on the comparison target M acquired by the acquisition unit 11, the distance between the two points on the comparison target M on the moving image captured by the image-capturing unit 13, and the positional relationship between the point on the left eye L of the subject SB and the two points on the comparison target M on the moving image captured by the image-capturing unit 13.

In the example in which the acquisition unit 11 does not acquire the actual size of the distance between the two points on the comparison target M, the analysis unit 14 analyzes the movement of the eyeball of the right eye R of the subject SB, based on the distance between the two points on the comparison target M on the moving image captured by the image-capturing unit 13, and the positional relationship between the point on the right eye R of the subject SB and the two points on the comparison target M on the moving image captured by the image-capturing unit 13.

Further, the analysis unit 14 analyzes the movement of the eyeball of the left eye L of the subject SB, based on the distance between the two points on the comparison target M on the moving image captured by the image-capturing unit 13, and the positional relationship between the point on the left eye L of the subject SB and the two points on the comparison target M on the moving image captured by the image-capturing unit 13.

For example, in the example in which the comparison target M is attached to the subject SB such that the side AB shown in FIG. 8D is included in the vertical line (that is, the side AD is included in the horizontal line), the analysis unit 14 can determine whether or not the inclination of the face of the subject SB has changed, based on the orientation of the comparison target M (rectangular sticker) on the moving image captured by the image-capturing unit 13. Specifically, the analysis unit 14 can determine the inclination of the face of the subject SB, based on the positional relationship between vertices A and B (or positional relationship between vertices A and D) of the comparison target M (rectangular sticker) on the moving image captured by the image-capturing unit 13.

That is, in this example, a rectangular sticker as the comparison target M is attached to the subject SB such that the inclination of the face of the subject SB can be determined from the moving image captured by the image-capturing unit 13.

Further, in this example, the analysis unit 14 determines the inclination of the face of the subject SB from the moving image captured by the image-capturing unit 13, by using two rectangular vertices A and B (or vertices A and D).

Figure 8E:
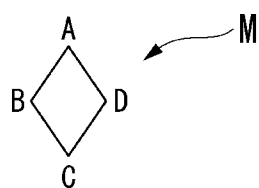

In the example shown in FIG. 8E, the comparison target M is a diamond-shaped sticker. The information of the comparison target M (diamond-shaped sticker) acquired by the acquisition unit 11 includes the actual size of the distance between two points (two vertices of the diamond shape) on the comparison target M (for example, the actual size of the diagonal line AC, the actual size of the diagonal line BD, and the like).

In the example shown in FIG. 8E, in order to analyze the movement of the eyeball of the right eye R of the subject SB, the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13 are used.

That is, the analysis unit 14 analyzes the movement of the eyeball of the right eye R of the subject SB, based on the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13.

Similarly, the analysis unit 14 analyzes the movement of the eyeball of the left eye L of the subject SB, based on the actual size of the distance between the two points on the comparison target M acquired by the acquisition unit 11, the distance between the two points on the comparison target M on the moving image captured by the image-capturing unit 13, and the positional relationship between the point on the left eye L of the subject SB and the two points on the comparison target M on the moving image captured by the image-capturing unit 13.

In the example in which the acquisition unit 11 does not acquire the actual size of the distance between the two points on the comparison target M, the analysis unit 14 analyzes the movement of the eyeball of the right eye R of the subject SB, based on the distance between the two points on the comparison target M on the moving image captured by the image-capturing unit 13, and the positional relationship between the point on the right eye R of the subject SB and the two points on the comparison target M on the moving image captured by the image-capturing unit 13.

Further, the analysis unit 14 analyzes the movement of the eyeball of the left eye L of the subject SB, based on the distance between the two points on the comparison target M on the moving image captured by the image-capturing unit 13, and the positional relationship between the point on the left eye L of the subject SB and the two points on the comparison target M on the moving image captured by the image-capturing unit 13.

For example, in the example in which the comparison target M is attached to the subject SB such that the diagonal line AC shown in FIG. 8E is included in the vertical line (that is, the diagonal line BD is included in the horizontal line), the analysis unit 14 can determine whether or not the inclination of the face of the subject SB has changed, based on the orientation of the comparison target M (the diamond-shaped sticker) on the moving image captured by the image-capturing unit 13. Specifically, the analysis unit 14 can determine the inclination of the face of the subject SB, based on the positional relationship between vertices A and C (or positional relationship between vertices B and D) of the comparison target M (diamond-shaped sticker) on the moving image captured by the image-capturing unit 13.

That is, in this example, a diamond-shaped sticker as the comparison target M is attached to the subject SB such that the inclination of the face of the subject SB can be determined from the moving image captured by the image-capturing unit 13.

Further, in this example, the analysis unit 14 determines the inclination of the face of the subject SB from the moving image captured by the image-capturing unit 13, by using two diamond-shaped vertices A and C (or vertices B and D).

Figure 8F:
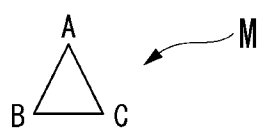
Figure 8G:
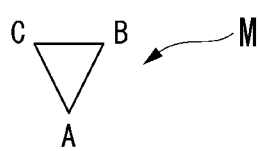

In the examples shown in FIGS. 8F and 8G, the comparison target M is a triangular sticker. The information of the comparison target M (triangular sticker) acquired by the acquisition unit 11 includes the actual size of the distance between two points (two vertices of the triangle) on the comparison target M (for example, the actual size of the side BC).

In the examples shown in FIGS. 8F and 8G, in order to analyze the movement of the eyeball of the right eye R of the subject SB, the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13.

That is, the analysis unit 14 analyzes the movement of the eyeball of the right eye R of the subject SB, based on the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13.

Similarly, the analysis unit 14 analyzes the movement of the eyeball of the left eye L of the subject SB, based on the actual size of the distance between the two points on the comparison target M acquired by the acquisition unit 11, the distance between the two points on the comparison target M on the moving image captured by the image-capturing unit 13, and the positional relationship between the point on the left eye L of the subject SB and the two points on the comparison target M on the moving image captured by the image-capturing unit 13.

In the example in which the acquisition unit 11 does not acquire the actual size of the distance between the two points on the comparison target M, the analysis unit 14 analyzes the movement of the eyeball of the right eye R of the subject SB, based on the distance between the two points on the comparison target M on the moving image captured by the image-capturing unit 13, and the positional relationship between the point on the right eye R of the subject SB and the two points on the comparison target M on the moving image captured by the image-capturing unit 13.

Further, the analysis unit 14 analyzes the movement of the eyeball of the left eye L of the subject SB, based on the distance between the two points on the comparison target M on the moving image captured by the image-capturing unit 13, and the positional relationship between the point on the left eye L of the subject SB and the two points on the comparison target M on the moving image captured by the image-capturing unit 13.

For example, in an example in which the comparison target M is attached to the subject SB such that the side BC shown in FIG. 8F is included in the horizontal line and the vertex A is located above the side BC, or, for example, in an example in which the comparison target M is attached to the subject SB such that the side BC shown in FIG. 8G is included in the horizontal line and the vertex A is located below the side BC, the analysis unit 14 can determine whether the inclination of the face of the subject SB has changed, based on the orientation of the comparison target M (triangular sticker) on the moving image captured by the image-capturing unit 13. Specifically, the analysis unit 14 can determine the inclination of the face of the subject SB, based on the positional relationship between the vertex A and the side BC of the comparison target M (triangular sticker) on the moving image captured by the image-capturing unit 13.

That is, in this example, a triangular sticker as the comparison target M is attached to the subject SB such that the inclination of the face of the subject SB can be determined from the moving image captured by the image-capturing unit 13.

Further, in this example, the analysis unit 14 determines the inclination of the face of the subject SB from the moving image captured by the image-capturing unit 13, by using the vertex A and the side BC of the triangle.

Figure 8H:
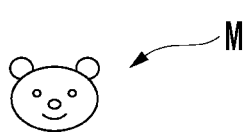

In the example shown in FIG. 8H, the comparison target M is a sticker of a figure (for example, a character figure) in which a plurality of straight lines, curves, and the like are combined. The information of the comparison target M (figure sticker) acquired by the acquisition unit 11 includes the actual size of the distance between two points on the comparison target M (for example, the right eye and the left eye of the character shown in FIG. 8H).

In the example shown in FIG. 8H, in order to analyze the movement of the eyeball of the right eye R of the subject SB, the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13 are used.

That is, the analysis unit 14 analyzes the movement of the eyeball of the right eye R of the subject SB, based on the actual size of the distance between the two points on the comparison target M acquired by the acquisition unit 11, the distance between the two points on the comparison target M on the moving image captured by the image-capturing unit 13, and the positional relationship between the point on the right eye R of the subject SB and the two points on the comparison target M on the moving image captured by the image-capturing unit 13.

Similarly, the analysis unit 14 analyzes the movement of the eyeball of the left eye L of the subject SB, based on the actual size of the distance between the two points on the comparison target M acquired by the acquisition unit 11, the distance between the two points on the comparison target M on the moving image captured by the image-capturing unit 13, and the positional relationship between the point on the left eye L of the subject SB and the two points on the comparison target M on the moving image captured by the image-capturing unit 13.

In the example in which the acquisition unit 11 does not acquire the actual size of the distance between the two points on the comparison target M, the analysis unit 14 analyzes the movement of the eyeball of the right eye R of the subject SB, based on the distance between the two points on the comparison target M on the moving image captured by the image-capturing unit 13, and the positional relationship between the point on the right eye R of the subject SB and the two points on the comparison target M on the moving image captured by the image-capturing unit 13.

Further, the analysis unit 14 analyzes the movement of the eyeball of the left eye L of the subject SB, based on the distance between the two points on the comparison target M on the moving image captured by the image-capturing unit 13, and the positional relationship between the point on the left eye L of the subject SB and the two points on the comparison target M on the moving image captured by the image-capturing unit 13.

For example, in the example in which the comparison target M is attached to the subject SB such that the right eye and the left eye of the character shown in FIG. 8H are located on the horizontal line (that is, the comparison target M is arranged as shown in FIG. 8H), the analysis unit 14 can determine whether or not the inclination of the face of the subject SB has changed, based on the orientation of the comparison target M on the moving image captured by the image-capturing unit 13. Specifically, the analysis unit 14 can determine the inclination of the face of the subject SB, based on the orientation of the face of the character of the comparison target M on the moving image captured by the image-capturing unit 13.

That is, in this example, the sticker of the figure as the comparison target M is attached to the subject SB such that the inclination of the face of the subject SB can be determined from the moving image captured by the image-capturing unit 13.

Further, in this example, the analysis unit 14 determines the inclination of the face of the subject SB from the moving image captured by the image-capturing unit 13 by using two points on the comparison target M.

Figure 9A:
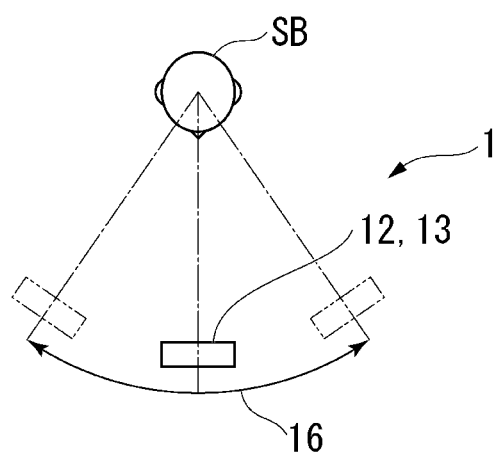
FIGS. 9A and 9B are diagrams showing a second application example of the eye movement analysis system of the first embodiment.
Figure 9B:
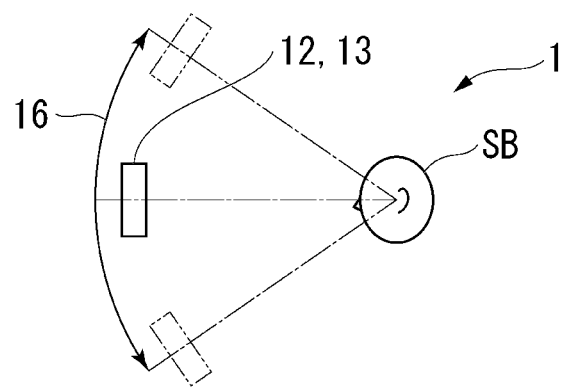

FIGS. 9A and B are diagrams showing a second application example of the eye movement analysis system 1 of the first embodiment. In detail, FIG. 9A shows an example of the relationship between the eye movement analysis system 1 and the subject SB in the horizontal plane, and FIG. 9B shows an example of the relationship between the eye movement analysis system 1 and the subject SB in the vertical plane.

In the example shown in FIGS. 9A and B, the eye movement analysis system 1 of the first embodiment includes a moving unit 16 in addition to the acquisition unit 11, the display unit 12, the image-capturing unit 13, the analysis unit 14, and the output unit 15.

The moving unit 16 integrally moves the display unit 12 and the image-capturing unit 13. Specifically, the moving unit 16 has a function of integrally moving the display unit 12 and the image-capturing unit 13 such that the distance between the display unit 12 and the image-capturing unit 13 and the subject SB does not change.

That is, as shown in FIG. 9A, the moving unit 16 can integrally move the display unit 12 and the image-capturing unit 13 along an arc centered on the subject SB (specifically, an arc on a horizontal plane). Further, as shown in FIG. 9B, the moving unit 16 can integrally move the display unit 12 and the image-capturing unit 13 along an arc centered on the subject SB (specifically, an arc on the vertical plane).

Further, the moving unit 16 can integrally move the display unit 12 and the image-capturing unit 13 along the surface of a sphere centered on the subject SB (specifically, a sphere having the same radius as the arc shown in FIGS. 9A and 9B).

As described above, in the first application example and the second application example of the eye movement analysis system 1 of the first embodiment, the acquisition unit 11, the analysis unit 14, and the output unit 15 of the eye movement analysis system 1 are configured by, for example, a personal computer as shown in FIG. 2A, the display unit 12 of the eye movement analysis system 1 is configured by a monitor (not shown), and the image-capturing unit 13 of the eye movement analysis system 1 is configured by, for example, a camera as shown in FIG. 2A.

In the third application example of the eye movement analysis system 1 of the first embodiment, the eye movement analysis system 1 is configured by, for example, a mobile terminal device (not shown) such as a smartphone or the like. Specifically, the acquisition unit 11 and the analysis unit 14 of the eye movement analysis system 1 are configured by a built-in computer (not shown) of a mobile terminal device. Further, the display unit 12 and the output unit 15 of the eye movement analysis system 1 are configured by a display (not shown) of a mobile terminal device. Further, the image-capturing unit 13 of the eye movement analysis system 1 is composed of a built-in camera (not shown) of the mobile terminal device.

That is, in the third application example of the eye movement analysis system 1 of the first embodiment, it can be used as an application in conjunction with a built-in camera such as a smartphone.

Second Embodiment

Hereinafter, a second embodiment of the eye movement analysis system, the eye movement analysis method, and the program of the present invention will be described.

The eye movement analysis system 1 of the second embodiment is configured in the same manner as the eye movement analysis system 1 of the first embodiment described above, except for the points described later. Therefore, according to the eye movement analysis system 1 of the second embodiment, the same effect as the effect of the eye movement analysis system 1 of the first embodiment described above can be obtained except for the points described later.

As described above, in the eye movement analysis system 1 of the first embodiment, the image-capturing unit 13 captures a moving image including the right eye R and the left eye L of the subject SB (see FIG. 2A) and the comparison target M.

On the other hand, in the eye movement analysis system 1 of the second embodiment, the image-capturing unit 13 captures a moving image including the right eye R of the subject SB and the comparison target M, or a moving image including the left eye L of the subject SB and the comparison target M.

As described above, in the eye movement analysis system 1 of the first embodiment, the analysis unit 14 analyzes the eyeball movements of the right eye R and left eye L of the subject SB, based on the information of the comparison target M and the moving image including the right eye R and left eye L of the subject SB and the comparison target M.

On the other hand, in the eye movement analysis system 1 of the second embodiment, the analysis unit 14 analyzes the movement of the eyeball of the right eye R of the subject SB, based on the information of the comparison target M and the moving image including the right eye R of the subject SB and the comparison target M, or analyzes the movement of the eyeball of the left eye L of the subject SB, based on the information of the comparison target M and the moving image including the left eye L of the subject SB and the comparison target M.

In the process executed in the eye movement analysis system 1 of the second embodiment, in step S1 of FIG. 3, the acquisition unit 11 acquires the information of the comparison target M attached to the surface of the face of the subject SB.

Further, in step S2 of FIG. 3, the display unit 12 displays an optotype.

Next, in step S3 of FIG. 3, the image-capturing unit 13 captures a moving image including, for example, the right eye R of the subject SB and the comparison target M.

Next, in step S4 of FIG. 3, based on the information of the comparison target M acquired in step S1 and the moving image including the right eye R of the subject SB and the comparison target M captured in step S3, the movement of the eyeball of the right eye R of the subject SB is analyzed.

Next, in step S5 of FIG. 3, the output unit 15 outputs the result of the analysis of the movement of the eyeball of the right eye R of the subject SB executed in step S4.

It is considered that the nystagmus analysis method using the eye movement analysis system, the eye movement analysis method and the program of the present invention becomes the standard of the nystagmus analysis method and can greatly contribute to the elucidation of the pathological condition of the nystagmus.

Further, according to the eye movement analysis system, the eye movement analysis method, and the program of the present invention, detailed nystagmus analysis in children becomes possible. By using the eye movement analysis system, eye movement analysis method, and program of the present invention, even an adult subject can undergo a nystagmus test that is simpler and much less burdensome than a nystagmus measuring device in the related art.

That is, according to the eye movement analysis system, the eye movement analysis method, and the program of the present invention, it is possible to significantly change the method of measuring nystagmus and the way of medical treatment of nystagmus.

Although the embodiments of the present invention have been described in detail with reference to the drawings, the specific configuration is not limited to these embodiments and can be appropriately modified without departing from the spirit of the present invention. The configurations described in each of the above-described embodiments and examples may be combined.

It should be noted that all or a part of the functions of each unit included in the eye movement analysis system 1 in the above-described embodiment may be realized by recording a program for realizing these functions on a computer-readable recording medium, loading the program recorded on the computer-readable recording medium into a computer system, and executing the program. The term "computer system" as used herein includes hardware such as an OS and peripheral devices.

Further, the "computer-readable recording medium" refers to a portable medium such as a flexible disk, a magneto-optical disk, a ROM, or a CD-ROM, or a storage unit such as a hard disk built in a computer system. Further, a "computer-readable recording medium" may include those which dynamically hold programs for a short period of time, such as a communication line when a program is transmitted via a network such as the Internet or a communication line such as a telephone line, or those which hold programs for a certain period of time, such as a volatile memory inside a computer system that serves as a server or client in that case. Further, the above-described program may be a program for realizing a part of the above-described functions, and may be a program for realizing the above-described functions in combination with a program already recorded in the computer system.

REFERENCE SIGNS LIST

1: Eye movement analysis system
11: Acquisition unit
12: Display unit
13: Image-capturing unit
14: Analysis unit
15: Output unit
16: Moving unit
SB: Subject
R: Right eye
RP: Pupil
RR: Iris
L: Left eye
M: Comparison target

What is claimed is:

1. An eye movement analysis system comprising:
an image-capturing unit configured to capture a moving image including at least one of a right eye and a left eye of a subject and a comparison target on a surface of a face of the subject;
an acquisition unit configured to acquire information of the comparison target; and
an analysis unit configured to analyze a movement of an eyeball of the at least one of the right eye and the left eye of the subject, based on a relationship between the at least one of the right eye and the left eye of the subject and the comparison target on the moving image captured by the image-capturing unit,
wherein the analysis unit is configured to analyze:
a movement of an eyeball of the right eye of the subject, based on an actual size of a comparison target acquired by the acquisition unit, the dimensions of the comparison target on the moving image captured by the image-capturing unit, and a distance relationship between the right eye of the subject and the comparison target on the moving image captured by the image-capturing unit, and
a movement of an eyeball of the left eye of the subject, based on an actual size of a comparison target acquired by the acquisition unit, the dimensions of the comparison target on the moving image captured by the image-capturing unit, and the distance between the left eye of the subject and the comparison target on the moving image captured by the image-capturing unit.

2. The eye movement analysis system according to claim 1, wherein the comparison target is a sticker attached between eyebrows of the subject.

3. The eye movement analysis system according to claim 1, wherein:

an actual size of a distance between a plurality of points on the comparison target is used as the actual size of the comparison target, and a dimension between the plurality of points on the comparison target on the moving image is used as the dimension of the comparison target on the moving image.

4. The eye movement analysis system according to claim 3, wherein:

the comparison target is circular, and the analysis unit analyzes:

the movement of the eyeball of the right eye of the subject, based on an actual size of a diameter or a radius of the comparison target acquired by the acquisition unit, the diameter or the radius of the comparison target on the moving image captured by the image-capturing unit, and a distance between a point on the right eye of the subject and a center of the comparison target on the moving image captured by the image-capturing unit, and the movement of the eyeball of the left eye of the subject, based on the actual size of the diameter or the radius of the comparison target acquired by the acquisition unit, the diameter or the radius of the comparison target on the moving image captured by the image-capturing unit, and a distance between a point on the left eye of the subject and the center of the comparison target on the moving image captured by the image-capturing unit.

5. The eye movement analysis system according to claim 4, wherein:

the point on the right eye of the subject on the moving image is a center of a pupil of the right eye of the subject on the moving image, and the point on the left eye of the subject on the moving image is a center of a pupil of the left eye of the subject on the moving image.

6. The eye movement analysis system according to claim 4, wherein:

the point on the right eye of the subject on the moving image is a point on an iris of the right eye of the subject on the moving image, and the point on the left eye of the subject on the moving image is a point on an iris of the left eye of the subject on the moving image.

7. The eye movement analysis system according to claim 4, wherein:

the point on the right eye of the subject on the moving image is a point on a conjunctival blood vessel of the right eye of the subject on the moving image, and the point on the left eye of the subject on the moving image is a point on a conjunctival blood vessel of the left eye of the subject on the moving image.

8. The eye movement analysis system according to claim 4, wherein:

the comparison target is polygonal, and the analysis unit analyzes:

the movement of the eyeball of the right eye of the subject, based on an actual size of a distance between two vertices of the polygon of the comparison target acquired by the acquisition unit, a distance between the two vertices of the polygon of the comparison target on the moving image captured by the image-capturing unit, and a positional relationship between a point on the right eye of the subject and the two vertices of the polygon of the comparison target on the moving image captured by the image-capturing unit, and the movement of the eyeball of the left eye of the subject, based on the actual size of the distance between the two vertices of the polygon of the comparison target acquired by the acquisition unit, the distance between the two vertices of the polygon of the comparison target on the moving image captured by the image-capturing unit, and a positional relationship between a point on the left eye of the subject and the two vertices of the polygon of the comparison target on the moving image captured by the image-capturing unit.

9. The eye movement analysis system according to claim 4, wherein:

the comparison target is polygonal, and the analysis unit analyzes:

the movement of the eyeball of the right eye of the subject, based on an actual size of a distance between two vertices of the polygon of the comparison target acquired by the acquisition unit, the distance between the two vertices of the polygon of the comparison target on the moving image captured by the image-capturing unit, and a positional relationship between two points on the right eye of the subject and the two vertices of the polygon of the comparison target on the moving image captured by the image-capturing unit, and the movement of the eyeball of the left eye of the subject, based on the actual size of the distance between the two vertices of the polygon of the comparison target acquired by the acquisition unit, the distance between the two vertices of the polygon of the comparison target on the moving image captured by the image-capturing unit, and a positional relationship between two points on the left eye of the subject and the two vertices of the polygon of the comparison target on the moving image captured by the image-capturing unit.

10. The eye movement analysis system according to claim 1, wherein:

the comparison target is a morphological feature on the surface of the face of the subject, and the analysis unit analyzes the movement of the eyeball of the at least one of the right eye and the left eye of the subject, based on a relationship between the at least one of the right eye and the left eye of the subject and two points on the comparison target on the moving image captured by the image-capturing unit.

11. The eye movement analysis system according to claim 10, wherein:

the analysis unit analyzes:

the movement of the eyeball of the right eye of the subject, based on a distance between the two points on the comparison target on the moving image captured by the image-capturing unit, and a positional relationship between a point on the right eye of the subject and the two points on the comparison target on the moving image captured by the image-capturing unit, and the movement of the eyeball of the left eye of the subject, based on the distance between the two points on the comparison target on the moving image captured by the image-capturing unit, and a positional relationship between a point on the left eye of the subject and the two points on the comparison target on the moving image captured by the image-capturing unit.

12. The eye movement analysis system according to claim 2, wherein the sticker as the comparison target is attached to the subject such that an inclination of a face of the subject is determined from the moving image captured by the image-capturing unit.

13. The eye movement analysis system according to claim 12, wherein the analysis unit determines the inclination of the face of the subject from the moving image captured by the image-capturing unit, by using at least two points on the sticker.

14. The eye movement analysis system according to claim 12, wherein the analysis unit determines the inclination of the face of the subject from the moving image captured by the image-capturing unit, by using a positional relationship between a plurality of stickers attached as the comparison target.

15. The eye movement analysis system according to claim 1, further comprising:
a display unit configured to display an optotype presented to the subject; and
a moving unit configured to integrally move the display unit and the image-capturing unit.

16. An eye movement analysis method comprising:
an image-capturing step of image-capturing a moving image including at least one of a right eye and a left eye of a subject and a comparison target on a surface of a face of the subject;
an acquisition step of acquiring information of the comparison target; and
an analysis step of analyzing:
a movement of an eyeball of the right eye of the subject, based on an actual size of a comparison target acquired by the acquisition step, the dimensions of the comparison target on the moving image captured by the image-capturing step, and a distance between the right eye of the subject and the comparison target on the moving image captured in the image-capturing step, and
a movement of an eyeball of the left eye of the subject, based on an actual size of a comparison target acquired by the acquisition step, the dimensions of the comparison target on the moving image captured by the image-capturing step, and a distance between the left eye of the subject and the comparison target on the moving image captured by the image-capturing step.

17. A program causing a computer to execute:
an image-capturing step of image-capturing a moving image including at least one of a right eye and a left eye of a subject and a comparison target on a surface of a face of the subject,
an acquisition step of acquiring information of the comparison target; and
an analysis step of analyzing:
a movement of an eyeball of the right eye of the subject, based on an actual size of a comparison target acquired by the acquisition step, the dimensions of the comparison target on the moving image captured by the image-capturing step, and a distance between the right eye of the subject and the comparison target on the moving image captured in the image-capturing step; and
a movement of an eyeball of the left eye of the subject, based on an actual size of a comparison target acquired by the acquisition step, the dimensions of the comparison target on the moving image captured by the image-capturing step, and a distance between the left eye of the subject and the comparison target on the moving image captured by the image-capturing step.

* * * * *